US012723055B2

(12) United States Patent
Mehellou et al.

(10) Patent No.: US 12,723,055 B2
(45) Date of Patent: Sep. 1, 2026

(54) PHOSPHOANTIGEN PRODRUG COMPOUNDS

(71) Applicants: UNIVERSITY COLLEGE CARDIFF CONSULTANTS LTD, Cardiff (GB); UNIVERSITY OF BIRMINGHAM, Birmingham (GB)

(72) Inventors: Youcef Mehellou, Cardiff (GB); Benjamin Willcox, Birmingham (GB)

(73) Assignees: University College Cardiff Consultants Ltd, Cardiff (GB); University of Birmingham, Birmingham (GB)

( * ) Notice: Subject to any disclaimer, the term of this patent is extended or adjusted under 35 U.S.C. 154(b) by 1130 days.

(21) Appl. No.: 17/256,272

(22) PCT Filed: Jul. 3, 2019

(86) PCT No.: PCT/GB2019/051880
§ 371 (c)(1),
(2) Date: Dec. 28, 2020

(87) PCT Pub. No.: WO2020/008189
PCT Pub. Date: Jan. 9, 2020

(65) Prior Publication Data

US 2021/0171552 A1 Jun. 10, 2021

(30) Foreign Application Priority Data

Jul. 4, 2018 (GB) ..................................... 1810965

(51) Int. Cl.

| | |
|---|---|
| ***C07F 9/44*** | (2006.01) |
| ***A61K 40/11*** | (2025.01) |
| ***A61K 40/42*** | (2025.01) |
| ***A61P 19/00*** | (2006.01) |
| ***A61P 35/00*** | (2006.01) |
| ***A61P 37/00*** | (2006.01) |
| ***A61P 37/04*** | (2006.01) |
| ***C12N 5/0783*** | (2010.01) |

(52) U.S. Cl.
CPC ............ *C07F 9/4465* (2013.01); *A61K 40/11* (2025.01); *A61K 40/42* (2025.01); *A61P 35/00* (2018.01); *A61P 37/04* (2018.01); *C12N 5/0636* (2013.01); *C12N 2501/999* (2013.01)

(58) Field of Classification Search
CPC ........ C07F 9/4465; C07F 9/44; A61K 31/664; A61P 35/00; A61P 37/00; A61P 37/04; A61P 19/00
See application file for complete search history.

(56) References Cited

U.S. PATENT DOCUMENTS

| | | | |
|---|---|---|---|
| 3,149,144 | A | 9/1964 | Huffman et al. |
| 5,747,332 | A | 5/1998 | Wallen et al. |
| 5,788,963 | A | 8/1998 | Murphy et al. |
| 6,274,378 | B1 | 8/2001 | Steinman et al. |
| 8,153,426 | B2 | 4/2012 | Moser et al. |
| 8,338,173 | B2 | 12/2012 | Moser et al. |
| 2005/0009008 | A1 | 1/2005 | Robinson et al. |
| 2005/0196385 | A1 | 9/2005 | Romagne et al. |
| 2006/0194755 | A1 | 8/2006 | Romagne et al. |
| 2008/0075732 | A1 | 3/2008 | Moser |
| 2009/0208517 | A1 | 8/2009 | Moser |

FOREIGN PATENT DOCUMENTS

| | | | | |
|---|---|---|---|---|
| WO | 99/33847 | A1 | 7/1999 | |
| WO | 2002008235 | A1 | 1/2002 | |
| WO | 2004085635 | A1 | 10/2004 | |
| WO | 2004/096237 | A | 11/2004 | |
| WO | 2006017954 | A1 | 2/2006 | |
| WO | 2007/014352 | A1 | 2/2007 | |
| WO | 2008/030843 | A1 | 3/2008 | |
| WO | 2012/150866 | A1 | 11/2012 | |
| WO | 2016022827 | A1 | 2/2016 | |
| WO | WO2019/182904 | * | 9/2019 | ............. A61P 37/02 |

OTHER PUBLICATIONS

Bessieres et al, Highly convergent synthesis and antiviral activity of (E)-but-2-enyl nucleoside phosphonoamidates, European Journal of Medicinal Chemistry 2018, 31, 146, 678-686. (Year: 2018).*
Ribot et al., γδ T Cells in Tissue Physiology and Surveillance, Nature Reviews Immunology, vol. 21, pp. 221-232 (Year: 2021).*
Silva-Santos et al., γδ T Cells: Pleiotropic Immune Effectors with Therapeutic Potential in Cancer, National Reviews Cancer, vol. 19 , No. 7, pp. 392-404 (Year: 2019).*
Cieslak et al., Gamma delta T cells and their immunotherapeutic potential in cancer, Biomarker Research, vol. 13, Article No. 51, pp. 1-23 (Year: 2025).*
Brandes, Marlene et al, "Flexible migration program regulates γδ T-cell involvement in humoral immunity", www.bloodjournal.org, Blood, Nov. 15, 2003, vol. 102, No. 10; pp. 3693-3701; © The American Society of Hematology.

(Continued)

*Primary Examiner* — Brenda L Coleman
(74) *Attorney, Agent, or Firm* — Patrick M. Torre; Stites & Harbison PLLC

(57) ABSTRACT

The invention relates to a compound of General Formula (I): wherein R1, R2, R3, R4 and R5 are as defined herein. Compounds and compositions comprising the same exhibit high serum stability and potent activation of the γδ T-cell immune response, so are suitable for use in immunotherapy. The invention also relates to methods of immunotherapy using the compounds of General Formula (I).

(I)

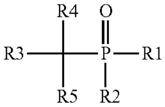

10 Claims, 17 Drawing Sheets

(56) References Cited

OTHER PUBLICATIONS

Figure 1:
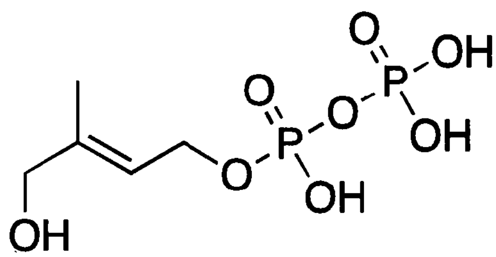
Figure 1:
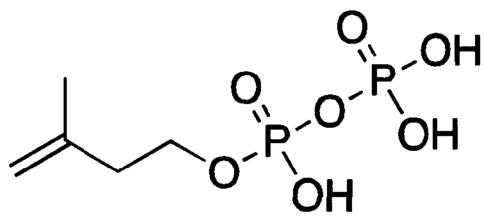
Figure 1:
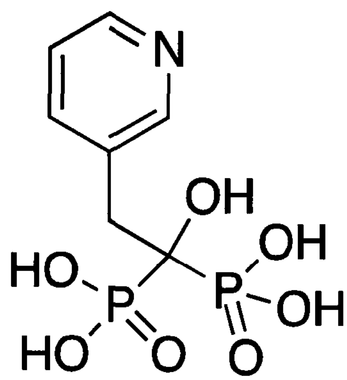
Figure 1:
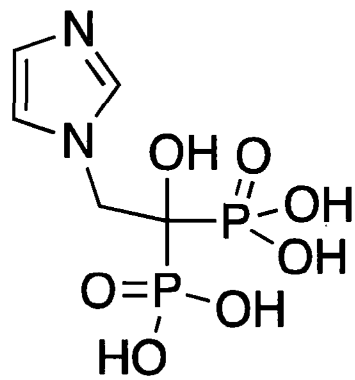

Moser, Bernhard et al, "γδ T cells: an alternative type of professional APC" , Trends in Immunology, Mar. 2006, vol. 27, pp. 112-118.
Hara, Toshiro et a; "Predominant Activation and Expansion of Vy9-bearing γδ T Cells In Vivo as well as In Vitro in *Salmonella* Infection", Journal of Clinical Investigation, vol. 9, pp. 204-210, 1992.
Yamanaka, Ryuya et al, "Clinical Evaluation of Dendritic Cell Vaccination for Patients with Recurrent Glioma: Results of a Clinical Phase 1/11 Trial", Clinical Cancer Research 2005, vol. 11, pp. 4160-4167.
Hintz, Martin et al, "Identification of (E)-4-hydroxy-3-methyl-but-2-enyl pyrophosphate as a major activator for human γδ T cells in *Escherichia coli* ", FEBS Letter, 2001, vol. 509, pp. 317-322.
Das, Hiranmoy et al, "MICA Engagement by Human V'Y2V62 T Cells Enhances Their Antigen-Dependent Effector Function" , Immunity, 2001, vol. 15, pp. 83-93.
Burgdorf, Sven and Kurts, Christian, "Endocytosis mechanisms and the cell biology of antigen presentation", Current Opinion in Immunology, 2008, vol. 20, pp. 89-95.
Efferson, Clay et al, "Stimulation of Human T Cells by an Influenza A Expressing a CTL Epitope from the HER-2/neu Protooncogene Results. in Higher Numbers of Antigen-specific TCRhi Cells than Stimulation with Peptide. Divergent Roles of IL-2 and IL-15", Anticancer Research 25, 2005, vol. 25, pp. 715-724.
Wheeler, "Preventive Vaccines for Cervical Cancer", Salud p'ublica de Mexico, Jul.-Aug. 1997, (4) 283-7.
Grossman, William and Oldfield, Eric, "Quantitative Structure-Activity Relations for γδ T Cell Activation by Phosphoantigens" , Journal of Medical Chemistry, 2002, vol. 45, No. 22, pp. 4868-4874.
Bieback, Karen et al., "Expansion of human γ/δ T cells in vitro is differentially regulated by the measles virus glycoproteins", Journal of General Virology, 2003, vol. 85, pt. 5, pp. 1179-1188.
Malkovska, Vera et al., "Antilymphoma Activity of Human γδ T-Cells in Mice with Severe Combined Immune Deficiency1" , Cancer Research, Oct. 15, 1992, vol. 52, pp. 5610-5616.
Bachman, Martin et al, "Recall Proliferation Potential of Memory cos+ T Cells and Antiviral Protection", Journal of Immunology, 2005, vol. 175, pp. 4677-4685.
Caccamo, Nadia et al, "XCR5 Identifies a subset of Vgamma9Vdelta2 T cells which secrete IL-4 and IL-10 and help B cells for antibody production", Journal of Immunology, vol. 177, 2006, pp. 5290-5295.
Brandes, Marlene et al: "Professional antigen-presentation function by human gamma delta T cells" Science (Washington DC). vol. 309, No. 5732, Jul. 2005 (Jul. 2005), pp. 264-268.
Modlin, Robert et al: "Immunology. Now presenting : gamma delta T cells." Science. vol. 309, No. 5732, Jul. 8, 2005 (Jul. 8, 2005), pp. 252-253.
Takamatsu, H-H et al: "A sub-population of circulating porcine gamma delta T cells can act as professional antigen presenting cells" Veterinary Immunology and Immunopathology,vol. 87, No. 3-4, Sep. 10, 2002 (Sep. 10, 2002), pp. 223-224.
Collins, Robert A et al: "Gamma delta T cells present antigen to CD4+ alpha beta T cells" Journal of Leukocyte Biology, vol. 63, No. 6, Jun. 1998 (Jun. 1998), pp. 707-714.
Morita, Craig T et al, "Direct presentation of nonpeptide prenyl pyrophosphate antigens to human gamma delta T cells." Immunity. vol. 3, No. 4, Oct. 1995 (Oct. 1995), pp. 495-507.
Lanzavecchia, Antonio et al, "T cells can present antigens such as HIV GP120 targeted to their own surface molecules" Nature (London), vol. 334, No. 6182, 1988, pp. 530-532.
Lanzavecchia, Antonio, "Receptor-mediated antigen uptake and its effect on antigen presentation to class II-restricted T Lymphocytes", Annual Review of Immunology, Annual Reviews Inc, US, vol. 8, 1990, pp. 773-793.
Toshiro Hara, et al., "Predominant Activation and Expansion of Vy9-bearing "γδTCells In Vivo as well as In Vitro in *Salmonella* Infection", Journal of Clinical Investigation, Jul. 1992, pp. 204-210, vol. 90.
Pileggi, E., et al., Expedient synthesis and biological evaluation of alkenyl acyclic nucleoside phosphonate prodrugs; Bioorganic & Medicinal Chemistry, vol. 26(12), 2018 with CAPLUS Abstract.
Bessieres, et al., Highly convergent synthesis and antiviral activity of (E)-but-2-enyl nucleoside phosphonoamidates; European Journal of Medicinal Chemistry, Vo1. 146, 2018.
Wei, Y., et al., Oral Delivery of Propofol with Methoxymethylphosphonic Acid as the Delivery Vehicle, Journal of Medicinal Chemistry, vol. 60(20), 2017.
UK IPO Search Report for GB 1807831.1 dated Jan. 22, 2019.
International Search Report and Written Opinion in PCT/GB2019/051880, dated Sep. 5, 2019.
WO0208235 English machine translation, 2002.
Yang, Hyeyeon, et al., Catalytic Enantioselective Friedel-Crafts Alkylations of Indoles with [alpha] Phosphoric Enones, Organic Letters 2007, vol. 9, No. 12 Jun. 1, 2007, pp. 2281-2284.
Helferich, B., et al., Uber Phostamsauren, II-Justus Liebigs Annalen der Chemie, vol. 670, No. 1, Dec. 1, 1963, pp. 48-57-original.
Helferich, B., et al., Uber Phostamsauren, II-Justus Liebigs Annalen der Chemie, vol. 670, No. 1, Dec. 1, 1963, English machine translation of Abstract.
Roelofs, A. J.; Jauhiainen, M.; Monkkonen, H.; Rogers, M. J.; Monkkonen, J.; Thompson, K. Peripheral blood monocytes are responsible for gammadelta T cell activation induced by zoledronic acid through accumulation of IPP/DMAPP. British journal of haematology 2009, 144, 245-50.
Bessieres, M.; Sari, O.; Roy, V.; Warszycki, D.; Bojarski, A. J.; Nolan, S. P.; Snoeck, R ; Andrei, G.; Schinazi, R. F.; Agrofoglio, L.A. Sonication-Assisted Synthesis of (E)-2-40 Methyl-but-2-enyl Nucleoside Phosphonate Prod rugs. ChemistrySelect 2016, 1, 3108-3813.
Shippy et al, "Phosphinophosphonates and Their Tris-pivaloyloxymethyl Prodrugs Reveal a Negatively Cooperative Butyrophilin Activation Mechanism", Journal of Medicinal Chemistry, American Chemical Society, Feb. 20, 2017, 60 (6), 2373-2382.
Chia-Hung et al, "Synthesis of a Phosphoantigen Prodrug that Potently Activates . . . Lymphocytes", Chemistry & Biology, NL, Elsevier, Jul. 24, 2014, 21(8), 945-954.
Ivanova et al, "Copper-Mediated Introduction of the CFPO(OEt) Motif . . . ", Chemistry A European Journal, Wiley-VCH, Nov. 14, 2017, 23(68), 17318-17338.
RN 1349346-47-9 Registry, Database Registry [Online] Chemical Abstract Service, Retrieved from STN, Dec. 6, 2011, Search Date : Apr. 28, 2023, "L-Alanine, N-[[3-[[4-[[(4R,5S,6S,7R)-3-[(3-cyano-4-methoxyphenyl)methyl] hexahydro-5,6-dihydroxy-2-oxo-4,7-bis(phenyl-methyl)-1H-1,3-diazepin-1-yl ]methyl]benzoyl]amino]propyl]phenoxyphosphinyl]-, ethyl ester".
RN 1347887-21-1 Registry, Database Registry [Online] Chemical Abstract Service, Retrieved from STN, Dec. 4, 2011, Search Date : Apr. 28, 2023, "L-Alanine, N-[[3-[[4-[[(4R,5S,6S,7R)-3-[(3-amino-1H-indazol-5-yl)methyl] hexahydro-5,6-dihydroxy-2-oxo-4,7-bis(phenylmethyl)-1H-1,3-diazepin-1-yl ]methyl]benzoyl]amino]propyl]phenoxyphosphinyl]-, ethyl ester".
Morita, C. T.; Jin, C.; Sarikonda, G.; Wang, H. Nonpeptide antigens, presentation mechanisms, and immunological memory of human Vgamma2Vdelta2 T cells: discriminating friend from foe through the recognition of prenyl pyrophosphate antigens. Immunol Rev 2007, 215, 59-76.
Shen, Y.; Zhou, D.; Qiu, L.; Lai, X.; Simon, M.; Shen, L.; Kou, Z.; Wang, Q.; Jiang, L.; Estep, J.; Hunt, R.; Clagett, M.; Sehgal, P. K.; Li, Y.; Zeng, X.; Morita, C. T.; Brenner, M.B.; Letvin, N. L.; Chen, Z. W. Adaptive immune response of Vgamma2Vdelta2+ T cells during mycobacterial infections. Science (New York, N. Y) 2002, 295, 2255-8.
Fisher, J. P.; Heuijerjans, J.; Yan, M.; Gustafsson, K.; Anderson, J. gammadelta T cells for cancer immunotherapy: A systematic review of clinical trials. Oncoimmunology 2014, 3, e27572.

(56) References Cited

OTHER PUBLICATIONS

Maraka, S.; Kennel, K. A. Bisphosphonates for the prevention and treatment of osteoporosis. BMJ (Clinical research ed.) 2015, 351, h3783.
Davey, M. S.; Malde, R.; Mykura, R. C.; Baker, A. T.; Taher, T. E.; Le Duff, C. S.; Willcox, B. E.; Mehellou, Y., Synthesis and Biological Evaluation of (E)-4-Hydroxy-3-methylbut-2-enyl Phosphate (HMBP) Aryloxy Triester Phosphoramidate Pro-drugs as Activators of Vgamma9/Vdelta2 T-Cell Immune Responses. J Med Chem 2018, 61, 2111-2117.
Vougioukalakis, G. C.; Grubbs, R. H. Rutheniumbased heterocyclic carbenecoordinated olefin metathesis catalysts. Chem Rev 2010, 110, 17 46-87.
McKenna, C. E.; Higa, M. T.; Cheung, N. H.; McKenna, M.-C. The facile dealkylation 35 of phosphonic acid dialkyl esters by bromotrimethylsilane. Tetrahedron Letters 1977, 18, 155-158.
Mehellou, Y. The ProTides Boom. ChemMedChem 2016, 11, 1114-6.
Osgerby, L.; Lai, Y. C.; Thornton, P. J.; Amalfitano, J.; Le Duff, C. S.; Jabeen, I.; Kadri, H.; Miccoli, A.; Tucker, J. H. R.; Muqit, M. M. K.; Mehellou, Y. Kinetin Riboside and Its ProTides Activate the Parkinson's Disease Associated PTEN- Induced Putative Kinase 1 (PINK1) Independent of Mitochondrial Depolarization. J Med Chem 2017, 60, 3518-3524.

* cited by examiner

HMBPP

IPP

Risedronate

Zoledronate

1

2

3a: R= Me, 3b: R = *i*Pr
3c: R = *t*Bu, 3d: R = Bn.

4a: R= Me, 4b: R = *i*Pr
4c: R = *t*Bu, 4d: R = Bn.

5

6

7

8a: R= Me, 8b: R = *i*Pr
8c: R = *t*Bu, 8d: R = Bn.

9a: R= Me, 9b: R = *i*Pr
9c: R = *t*Bu, 9d: R = Bn.

PHOSPHOANTIGEN PRODRUG COMPOUNDS

This application is the national stage of international patent application no. PCT/GB2019/051880 filed on Jul. 3, 2019, which in turn claims priority from Great Britain Patent Application No. 1810965.2 filed on Jul. 4, 2018, the disclosures of which are incorporated herein by reference in their entirety.

TECHNICAL FIELD

The invention relates to a Phosphoantigen (PAg) prodrug compound and a pharmaceutical composition that exhibits high serum stability and potent activation of the γδ T-cell immune response. The compound and composition are for use in immunotherapy, and particularly for the treatment of infection, cancer, osteoporosis and other proliferative diseases. Also provided is a method of immunotherapy, comprising the use of the compound or composition according to the invention in order to activate a γδ T-cell immune response.

BACKGROUND

Present since birth and the dominant subtype of human γδ T-cells in adult peripheral blood, Vγ9/Vδ2 T-cells are now established as a key subset of γδ T-cells that is involved in the fight against many diseases such as tuberculosis, leprosy, typhoid, malaria, and toxoplasmosis[1]. Studies in primate models have also implicated Vγ9/Vδ2 T-cells in immunity to *Mycobacterium tuberculosis*[2]. These cells have also shown an ability to target and lyse a diverse range of cancer cells in vitro[1]. Together, these observations have made the Vγ9/Vδ2 subset a major focus in the therapeutic exploitation of γδ T-cells[3].

To date, a number of small molecule activators of Vγ9/Vδ2 T-cells have been reported. Among these are the naturally-occurring PAgs (E)-4-hydroxy-3-methylbut-2-enyl pyrophosphate (HMBPP) and isopentenyl pyrophosphate (IPP), and the two synthetic molecules, risedronate and zoledronate (FIG. 1), which are currently used in the clinic to treat osteoporosis and some types of cancer[4,5,6].

The most potent Vγ9/Vδ2 T-cells activator reported to date is HMBPP, $EC_{50}$=0.00051 μM, which activates these T-cells by binding the type-1 transmembrane protein butyrophilin 3A1. Although the binding site for these PAgs remained unclear amid conflicting reports as to whether they bind the extracellular or intracellular domains of this transmembrane protein, there is now compelling evidence that supports the notion that HMBPP binds the intracellular B30.2 domain of butyrophilin 3A1.

Encouraged by the potency of the HMBPP in activating Vγ9/Vδ2 T-cells, aryloxy triester phosphoramidate prodrug technology was recently applied to the monophosphate derivative of HMBPP, i.e. HMBP, as means to improve its drug-like properties[6]. In this prodrug approach, the monophosphate group is masked by an aryl group and/or an amino acid ester (FIG. 2), which are both enzymatically cleaved off inside cells to release the monophosphate or monophosphonate species. As such compounds are prodrugs of PAqs, they are termed ProPAgens to distinguish them from ProTides, which are prodrugs of nucleotides.

Whilst these HMBP ProPAgens exhibited potent activation of Vγ9/Vδ2 T-cells ($EC_{50}$=0.45-11 nM), their serum stability was rather low, primarily due to the cleavage of the —P—O— bond of these active compounds[6]. Therefore, it is an object of the present invention to design alternative ProPAgens that retain potent activation of Vγ9/Vδ2 T-cells whilst addressing the poor serum stability of previously reported HMBP ProPAgens active compounds.

SUMMARY

According to a first aspect of the invention there is provided a compound according to General Formula (I) including all tautomers thereof:

(I)

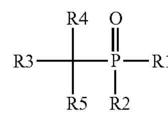

wherein R1 and R2 each independently represents an amino acid ester radical according to General Formula (II) or an aryloxy radical according to General Formula (III):

(II)

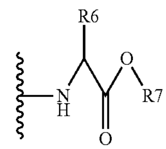

(III)

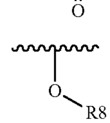

wherein R6 represents H, or a saturated or unsaturated and optionally substituted hydrocarbon chain;

R7 represents a saturated or unsaturated and optionally substituted hydrocarbon chain; and R8 represents an optionally substituted $C_{5-25}$ aryl or a 5 to 25 membered heteroaryl group;

R3 represents an optionally substituted $C_{2-20}$ alkyl, $C_{4-20}$ alkenyl or $C_{2-20}$ alcohol radical; and R4 and R5 each independently represent H or a halogen atom;

or a salt thereof.

In contrast to the conventional phosphate group-containing ProPAgens discussed above, Compounds of General Formula (I) include a phosphonate group that is masked by aryl and/or amino acid ester groups, which are enzymatically cleaved off inside cells to release an active phosphonate compound. It has been shown that the replacement of the labile —O—P— bond with a —C—C— bond resulted in a significant improvement in stability of the active phosphonate compound, which was shown to be a potent activator of Vγ9/Vδ2 T-cells. Further, this activity was translated to potent lysis of bladder cancer cells in vitro.

As Compounds of General Formula (I) have been shown to activate, with high specificity, Vγ9/Vδ2 T-cells, they are ideal candidates for development as immunotherapeutics. In particular, Compounds of General Formula (I) are useful for the treatment of infection, proliferative diseases such as cancer, and/or osteoporosis.

Suitable infections for treatment by Vγ9/Vδ2 T-cell activation immunotherapy include bacterial, viral and fungal infections. Particularly suitable infections are bacterial infections, especially of the *Mycobacterium* genus and/or *Salmonella enterica* species. Therefore, the compounds of General Formula (I) are particularly useful for the treatment of one or more of tuberculosis, leprosy and typhoid.

Alternatively, the infection may be a parasitic infection. Particularly suitable parasitic infections are of the *Plasmodium* genus and/or the *Toxoplasma* genus. Therefore, the compounds of General Formula (I) are particularly useful for the treatment of one or both of malaria and toxoplasmosis.

The compounds of general formula (I) are particularly useful for the treatment of cancer, in particular bladder, prostate, lung, neck, skin and breast cancers as well as mesothelioma.

The term 'halo' as used herein refers to fluoro, chloro, bromo or iodo, more suitably fluoro or chloro, and most suitable fluoro.

The term '$C_{2-20}$ alkyl' as used herein refers to a straight or branched saturated hydrocarbon chain containing from 2 to 20 carbon atoms. Examples include ethyl, n-propyl, isopropyl, n-butyl, s-butyl, t-butyl, n-hexyl, n-octyl and n-decyl.

The term '$C_{4-20}$ alkenyl' as used herein refers to a straight or branched unsaturated hydrocarbon chain containing 4 to 20 carbon atoms. Examples include butenyl, pentenyl etc.

The term '$C_{2-20}$ alcohol' as used herein refers to a straight or branched and saturated or unsaturated hydrocarbon chain containing 2 to 20 carbon atoms and including one or more hydroxyl (OH) functional group.

The term 'saturated or unsaturated hydrocarbon chain' as used herein refers to an aliphatic or aromatic hydrocarbon radical that may or may not include within said chain one or more double or triple bonds. Therefore, this term encapsulates alkyl, alkenyl alkynyl or aryl radicals.

The term '$C_{5-25}$ aryl' as used herein refers to any hydrocarbon group that contains 5 to 25 carbon atoms and includes one or more carbocyclic aromatic ring. More suitably aryl groups are $C_{6-14}$ and are preferably $C_{6-10}$ aryl groups.

The term 'heteroaryl' as used herein refers to any hydrocarbon group that includes one or more aromatic ring that includes one or more heteroatom (e.g. N, O or S) as part of said ring. Particularly suitable examples of heteroaryl groups are pyridine, furan, thiophene and indole groups. A 5 to 25 membered heteroaryl group refers to a group in which the total number of ring forming atoms (carbon and heteroatom(s)) is from 5 to 25.

Other alkyl, alkenyl, aryl and/or alcohol groups are as defined but have different numbers of carbon atoms. For example, $C_1$-4 alkyl has 1 to 4 carbon atoms.

The hydrocarbon chain and/or the aryl, heteroaryl, alkyl, alkenyl or alcohol radical may be optionally substituted with one or more heteroatom (e.g. O, S, or N) containing functional group. Examples of suitable heteroatom containing groups include, but are not limited to, nitro, nitrone, halo, amino, amido, cyano, carboxyl, sulphonyl, hydroxyl, alkoxy, ketone, aldehyde, thiol, thioether, and non-aromatic heterocyclic groups. The hydrocarbon chain may or may not contain a saturated or unsaturated cyclic ring(s). As used herein, any carbon number of a hydrocarbon chain, alkyl, alkenyl, aryl or alcohol radical includes any carbon atoms present in substituents. In preferred embodiments, the hydrocarbon chain and/or the aryl, heteroaryl, alkyl, alkenyl or alcohol radical are optionally substituted with one or more heteroatom containing functional group selected from thiol, thioether, alkoxy and amino (which may be a primary or secondary amino group).

Salts of the compounds of General Formula (I) are suitably pharmaceutically or veterinary acceptable salts. Depending on the nature of $R^1$ to $R^8$, these may be basic addition salts such as sodium, potassium, calcium, aluminium, zinc, magnesium and other metal salts as well as choline, diethanolamine, ethanolamine, ethyl diamine, megulmine and other well-known basic addition salts as summarised in Paulekuhn et al., (2007) *J. Med. Chem.* 50: 6665-6672 and/or known to those skilled in the art. Alternatively, when the compound of general formula (I) contains an amino group, this may be quaternised to form a salt with a counter ion such as halide, hydroxide, sulfate, nitrate, phosphate, formate, acetate, trifluoroacetate, fumarate, citrate, tartrate, oxalate, succinate, mandelate, methane sulfonate and p-toluene sulfonate.

In a preferred subset of compounds according to General Formula (I), the phosphonate group is masked by an amino acid ester and an aryl group. Such compounds are of General Formula (IV), wherein R3, R4, R5, R6, R7 and R8 are as defined above:

(IV)

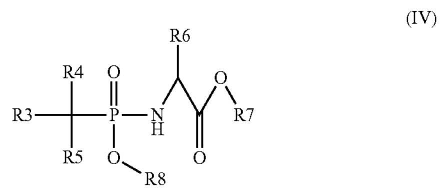

In some compounds of General Formula (I) or General Formula (IV), R3 is a $C_{4-16}$, and preferably a $C_{4-8}$, alkyl, alkenyl or alcohol radical. More preferably, R3 is an alcohol radical as defined above.

In particularly preferred compounds, R3 is a radical according to Formula (V), Formula (VI) or Formula (VII), wherein R9 is selected from OH, $OR^{10}$, SH, $SR^{10}$, $NH_2$ or $NHR^{10}$ and is preferably OH, and wherein $R^{10}$ represents $C_{1-4}$ alkyl:

(V)

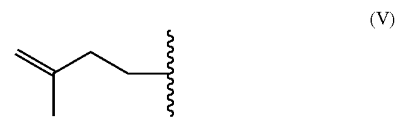

(VI)

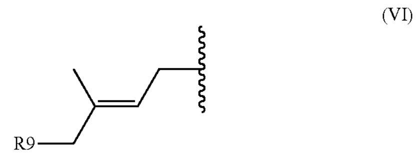

(VII)

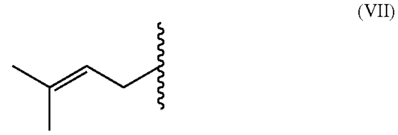

These R3 substituents are analogous to those found in the naturally-occurring PAgs IPP (Formula (V)), HMBPP (Formula (VI)) and the IPP isomer dimethylallyl diphosphate DMAPP Formula (VII)).

In particularly preferred embodiments, R3 is a radical according to Formula (VI).

As noted above, the compounds of General Formula (I) or General Formula (IV) comprise a masked phosphonate group, which includes a —C(R4)(R5)-P— bond, which is shown to be more stable than the —O—P— bond of conventional ProPAgens. In preferred embodiments, at least one, and more preferably both, of R3 and R5 represent halo.

Figure 3:
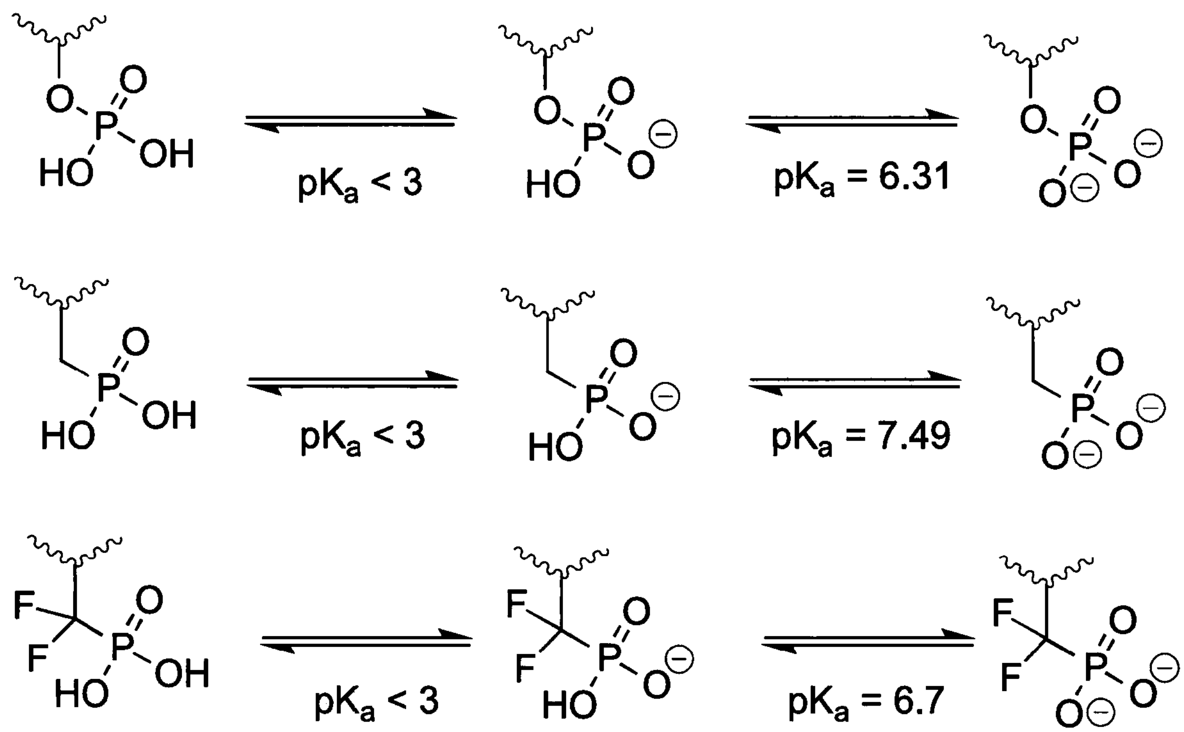

Although the change from a —O—P— bond to a —$CH_2$—P— bond has been shown to achieve better serum stability of the active compound, the $pK_a$ value for the second deprotonation of the phosphonate group ($pK_a$=7.49) is significantly different from that of the phosphate group ($pK_a$=6.31) (FIG. 3). This as a result affects the full ionization of the active compound under physiological pH (<7.4) and hence the binding affinity to the target protein, which requires the full ionization of the phosphate group to bind a positively charged pocket (arginine-rich) on the butyrophilin 3A1 intracellular domain.

However, it has been found that, by providing a difluoromethyl phosphonate (—$CF_2$—P—) bond, the active compounds combine excellent stability in physiological environments with a $pK_a$ value for the second deprotonation (6.7) very close to that of the second deprotonation of the native phosphate compound itself (FIG. 3). Therefore, the mono and/or dihalomethyl phosphonate derivatives of compounds according to General Formula (I) or (IV) combine excellent stability with potent activation of Vγ9/Vδ2 T-cells.

The compounds of General Formula (I) or (IV) are prodrugs in which the monophosphonate group is masked by an aryl group and/or an amino acid ester, which are both enzymatically cleaved off inside cells to release the active monophosphonate species.

Suitable amino acid ester masking groups include a wide variety of amino acid sidechain (R6) groups. Typically, R6 represents is a sidechain, preferably a nonpolar sidechain, of a proteinogenic amino acid. Particularly preferred R6 groups comprise a $C_{1-4}$ alkyl chain. Examples of such R6 groups include —$CH_3$ (Alanine), —$CH(CH_3)_2$ (Valine), —$CH_2CH(CH_3)_2$ (Leucine), —$CH(CH_3)CH_2CH_3$ (Isoleucine) and —$CH_2CH_2SCH_3$ (Methionine). Compounds in which R6 represents a methyl ($CH_3$) are particularly suitable.

R7 is a saturated or unsaturated and optionally substituted hydrocarbon chain and may be aliphatic or aromatic. Preferably, R7 is a 01-6 alkyl or $C_{6-14}$ aryl group. In particularly preferred embodiments R7 is $C_{6-10}$ aryl group, and is most preferably a benzyl group. Compounds according to General Formula (I) or (IV) comprising a benzyl ester have a higher rate of degradation and improved lipophilicity (and thus improved cell uptake) in comparison with aliphatic ester-based compounds.

Some particular suitable Compounds of General Formula (IV) include the following compounds:

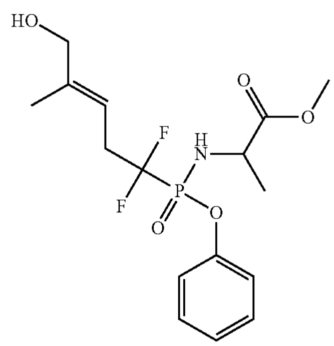

-continued

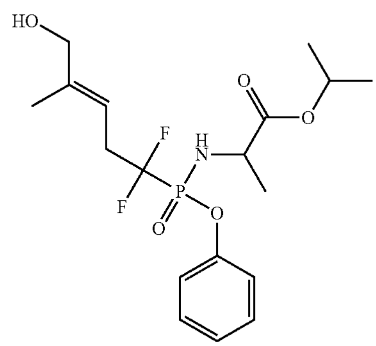

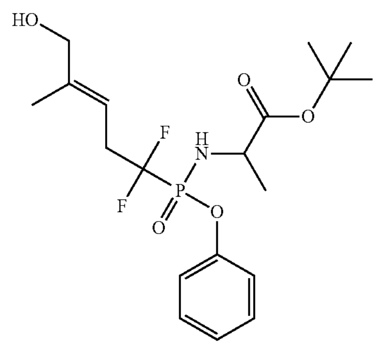

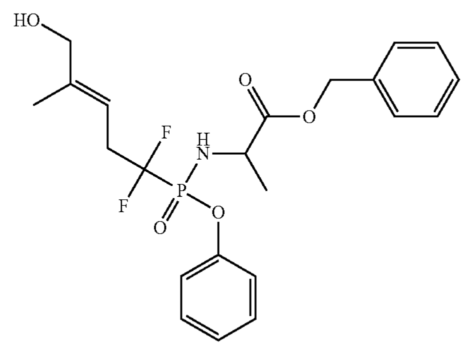

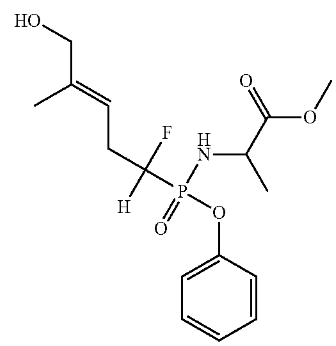

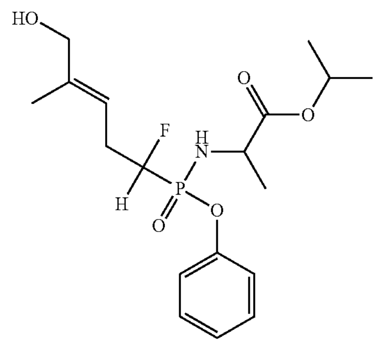

-continued

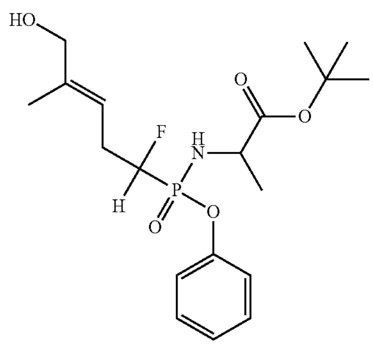

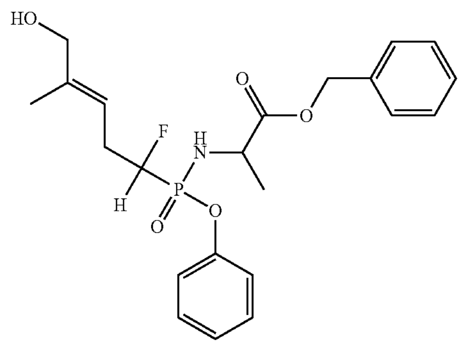

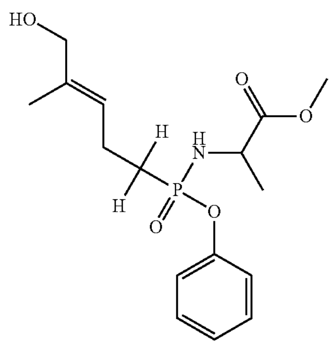

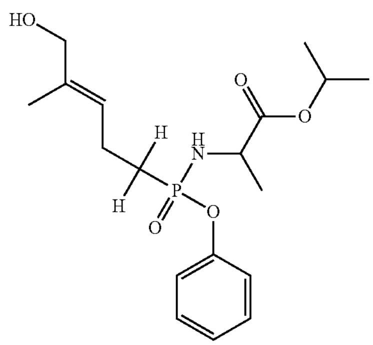

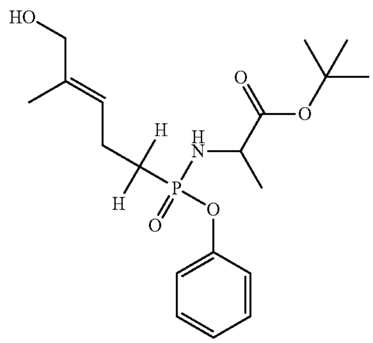

-continued

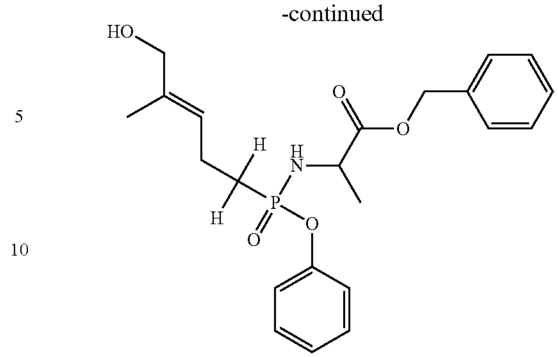

It will be appreciated that the compounds of the first aspect of the invention will generally be administered as part of a pharmaceutical composition. Therefore, according to a second aspect of the invention there is provided a pharmaceutical comprising a compound of the first aspect of the invention and a pharmaceutically acceptable excipient or carrier.

Suitable pharmaceutical excipients are well known to those of skill in the art. Pharmaceutical compositions may be formulated for administration by any suitable route, for example oral, rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy.

The composition may be prepared by bringing into association the compound of the first aspect of the invention with the carrier. In general, the formulations are prepared by uniformly and intimately bringing into association said compound with liquid carriers or finely divided solid carriers or both, and then if necessary shaping the product.

Formulations for oral administration in the present invention may be presented as: discrete units such as capsules, sachets or tablets each containing a predetermined amount of the compound; as a powder or granules; as a solution or a suspension of the compound in an aqueous liquid or a non-aqueous liquid; or as an oil-in-water liquid emulsion or a water-in-oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the compound in a free-flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Parenteral formulations will generally be sterile.

For topical application to the skin, the composition may be made up into a cream, ointment, jelly, solution or suspension etc. Cream or ointment formulations that may be used for the drug are conventional formulations well known in the art, for example, as described in standard textbooks of pharmaceutics such as the British Pharmacopoeia.

In a preferred embodiment of this aspect of the invention the composition is formulated for oral delivery.

The precise amount of a composition as defined herein which is therapeutically effective, and the route by which such compound is best administered, is readily determined by one of ordinary skill in the art. Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The doses of the compound or composition according to the invention administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

As mentioned above, the compounds of the first aspect of the invention represent prodrugs of highly stable potent activators of Vγ9/Vδ2 T-cells. Therefore, according to a third aspect of the invention, there is provided a compound of the first aspect or a pharmaceutical composition according to the second aspect for use in immunotherapy. In particular, and as already indicated above, the compounds or compositions are for use in the treatment of an infection, a proliferative disease such as cancer and/or osteoporosis.

According to a fourth aspect, the invention extends to a method of immunotherapy, the method comprising administering an effective amount of a compound according to the first aspect or a pharmaceutical composition according to the second aspect to activate a γδ T-cell immune response.

In a preferred method the compound or pharmaceutical composition of the invention is administered to a subject in need of such treatment by any suitable means. As will be appreciated, in this manner activation of a γδ T-cell immune response occurs in vivo to bring about an immune response.

Alternatively, there is a provided an ex vivo method wherein the compound or composition may be administered ex vivo to a sample obtained from an individual in need of treatment to induce proliferation of γδ T cells prior to said sample being returned to the body. For example, said sample includes but is not limited to a sample of Peripheral Blood Mononuclear Cells (PBMCs) from blood sample from the individual, wherein administration of the compound or composition brings about expansion and activation of γδ T-cell prior to return to the body of said individual.

The method of immunotherapy may be carried out to treat an infection, a proliferative disease or osteoporosis. In particular, the method may be used to treat cancer, especially bladder cancer, and/or the treatment of any of the following infections: tuberculosis, leprosy, typhoid, malaria, and toxoplasmosis.

There is also provided the use of a compound according to the first aspect or a pharmaceutical composition according to the second aspect in the preparation of an agent for the treatment of infection, cancer or other proliferative diseases or osteoporosis in a subject.

In a preferred embodiment of this aspect of the invention, said subject is a mammal. Ideally said mammal is human.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWING FIGURES

The Invention will now be described by way of example only with reference to the Examples below and to the following Figures wherein:

FIG. 1: Chemical structures of reported small molecule Vγ9/Vδ2 T-cells activators: Naturally-occurring PAgs (E)-

4-hydroxy-3-methyl but-2-enyl pyrophosphate (HMBPP) and isopentenyl pyrophosphate (IPP); Synthetic molecules risedronate and zoledronate.

Figure 2:
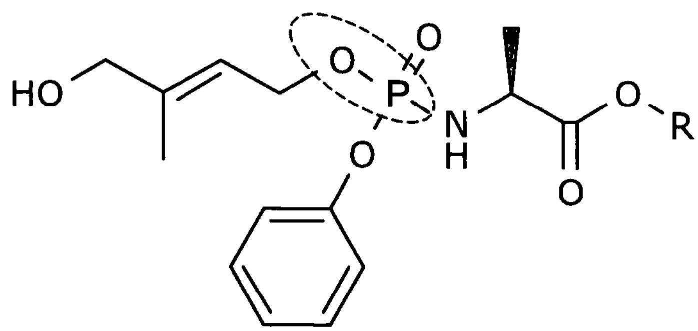

FIG. 2: Application of the aryloxy triester phosphoramidate prodrug technology to the monophosphate derivative of HMBPP (HMBP). The monophosphate group is masked by an aryl group and an amino acid ester, which are both enzymatically cleaved off inside cells to release the active monophosphate species. Instability was observed due to the cleavage of the —P—O— bond of these compounds (shaded).

FIG. 3: pKA values of phosphate and different phosphonate groups.

Figure 4A:
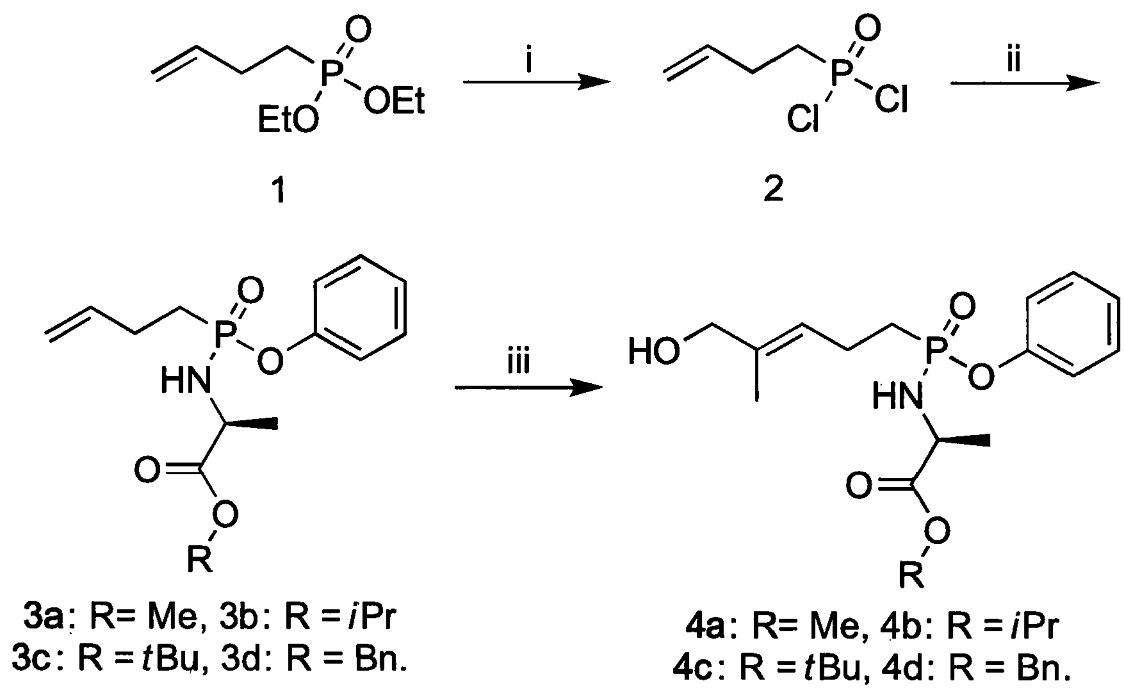
Figure 4B:
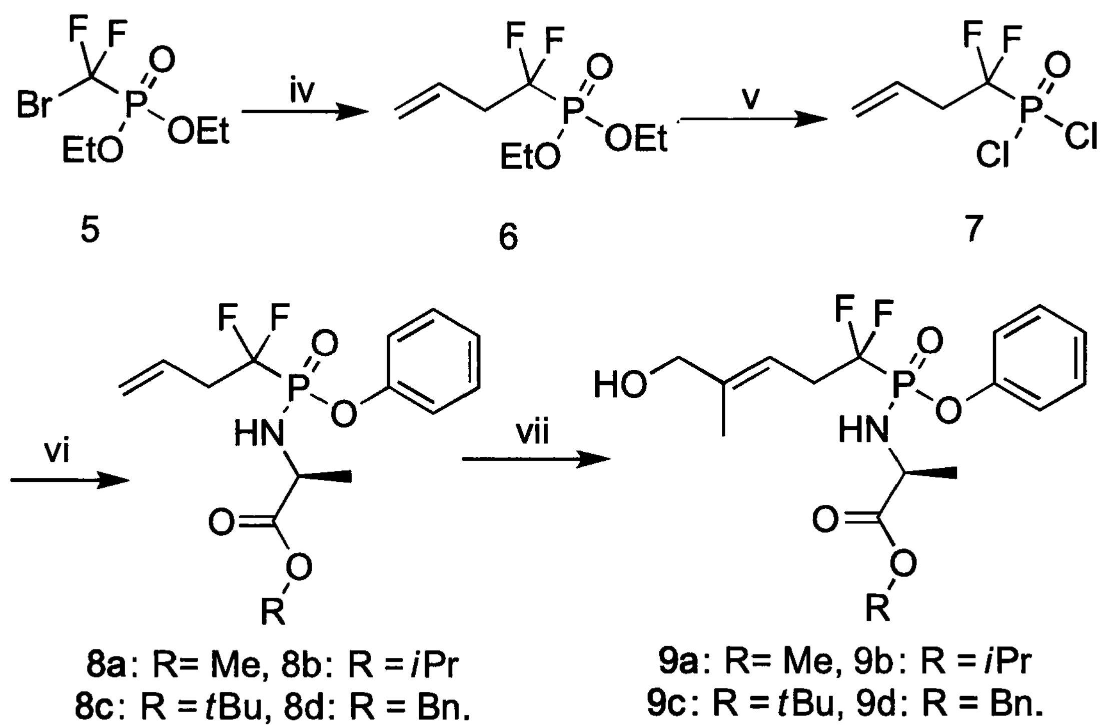

FIG. 4: Synthesis of (A) aryloxy phospharamidate ProPAgens of HMBP methylphosphonate (4a-d); and (B) HMBP difluoromethylphosphonate (9a-d). Reagents and conditions: (i) TMSBr, DCM, rt, 2 h then $(COCl)_2$, DMF cat, DCM, rt, 18 h; ii) a. Phenol, $Et_3N$, DCM, −78° C. for 30 mins then rt, 3 h; b. Substituted L-alanine ester hydrochloride, $Et_3N$, DCM, rt, 12 h, yields: 38-61%; (iii) 2-methyl-2-propenol, 1,4-benzoquinone, Hoveyda-Grubbs Catalyst $2^{nd}$ generation, DCM, rt, yields: 57-64%; (iv) Diethyl (bromodifluoromethyl)phosphonate, DMF, zinc powder, rt, $N_2$, 3h then CuBr, allyl bromide, rt, 40 h; (v) (i) TMSBr, DCM, rt, 2 h then $(COCl)_2$, DMF cat, DCM, rt, 18 h; ii) a. Phenol, $Et_3N$, DCM, −78° C. for 30 mins then rt, 3 h; b. Substituted L-alanine ester hydrochloride, $Et_3N$, DCM, rt, 12 h, yields: 24-46%; (iii) 2-methyl-2-propenol, 1,4-benzoquinone, Hoveyda-Grubbs Catalyst 2nd generation, DCM, rt, yields: 58-69%.

Figure 5:
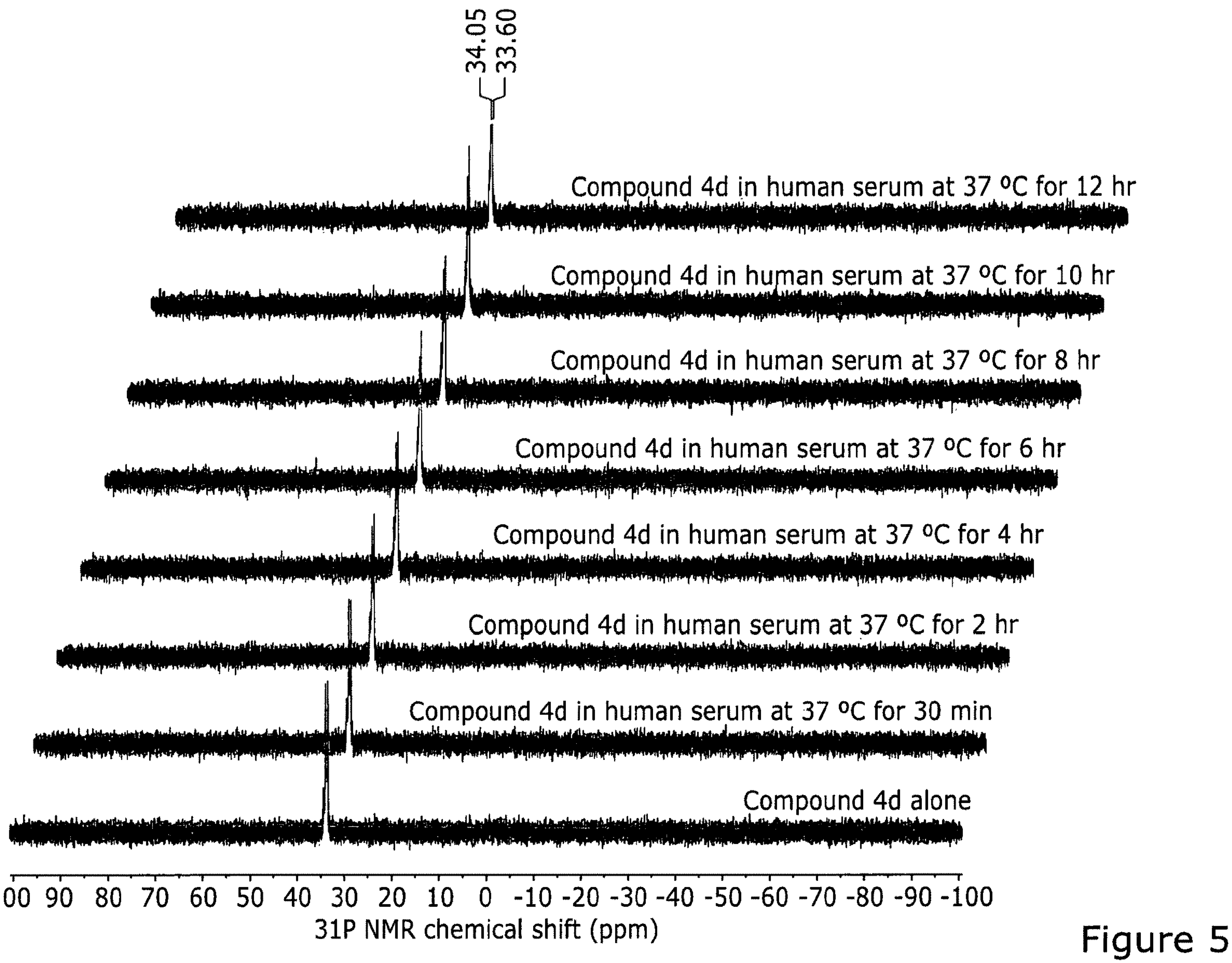

FIG. 5: Stability of HMBP phosphonate ProPAgen 4d in human serum at 37° C. for 12 hours as monitored by $^{31}P$ NMR. Prodrug 4d (5.0 mg) was dissolved in DMSO-$d_6$ (0.10 mL) and $D_2O$ (0.15 mL). All $^{31}P$ NMR spectra were recorded at 37° C. Initially, a $^{31}P$ NMR scan of prodrug 4d (5.0 mg) in DMSO-$d_6$ (0.10 mL) and $D_2O$ (0.15 mL) was recorded (shown as compound 4d alone in the figure). Following this, a previously defrosted human serum (0.30 mL) was added to the NMR tube and a spectrum immediately run. Spectra were recorded at 30 min after the addition and then at even time intervals over 12 hr.

Figure 6:
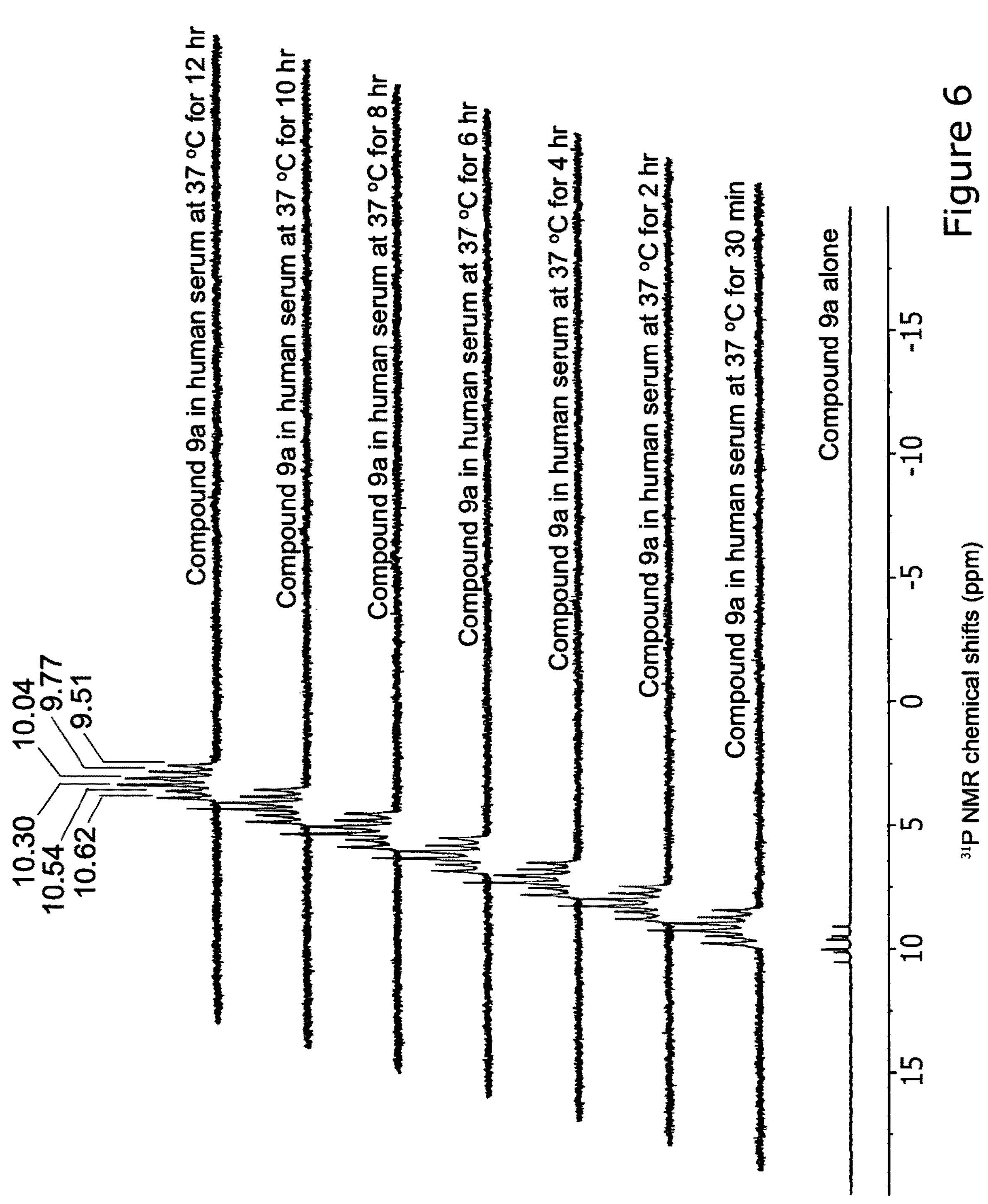

FIG. 6: Stability of HMBP phosphonate ProPAgen 9a in human serum at 37° C. for 12 hours as monitored by $^{31}P$ NMR. Same as for compound 4d above. The $^{31}P$ NMR of prodrug 9a shows six phosphorous peaks because of the coupling between the fluorine-phosphorous. In fact, these are eight peaks as predicted and two extra peaks are seen when zoomed into these peaks to make the predicted eight phosphorous peaks of such compounds.

Figure 7:
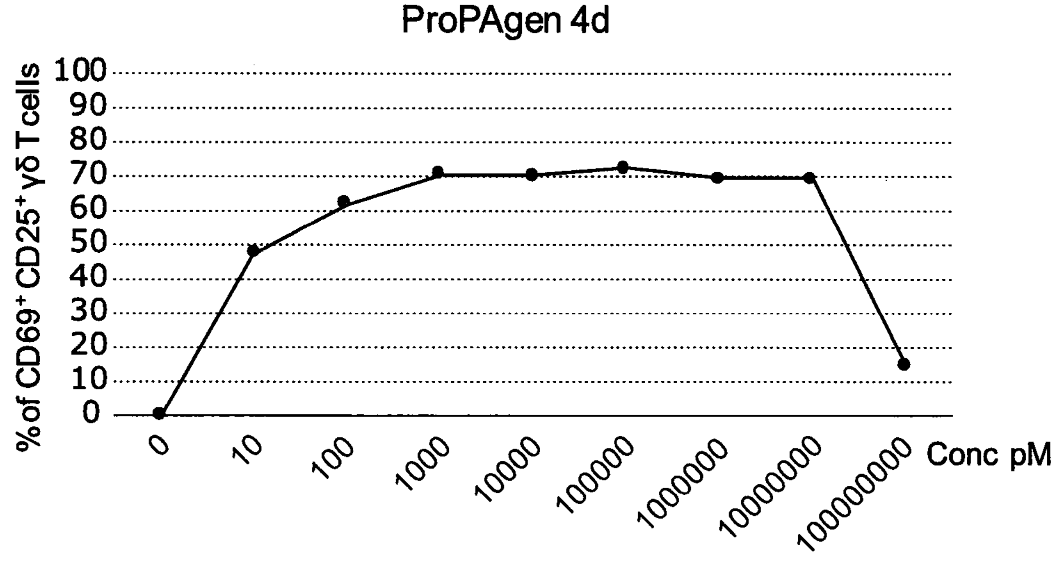
Figure 7:
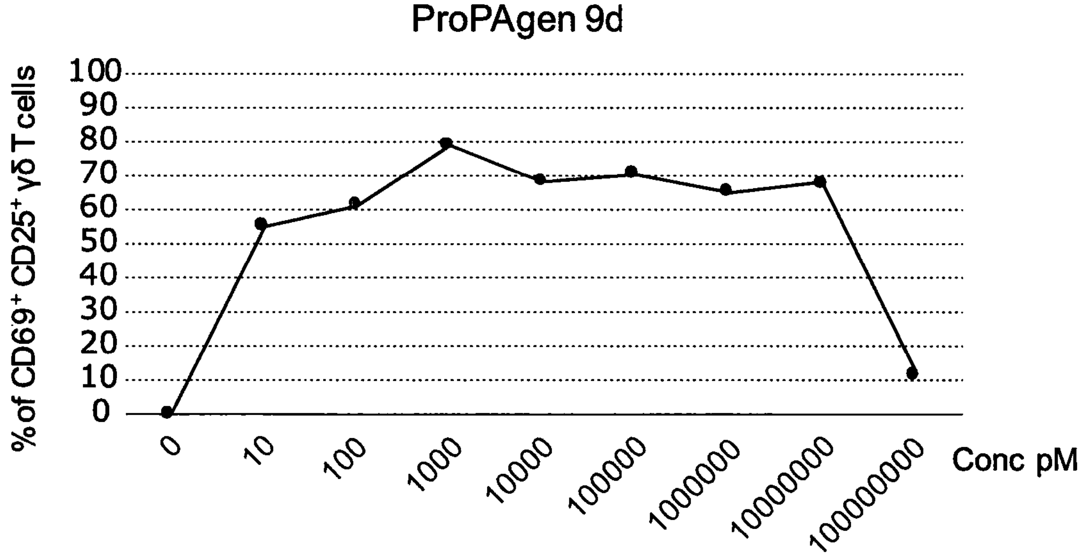

FIG. 7. Activation of human Vγ9/Vδ2⁺ T cells by HMBP phosphonate ProPAgens 4d and 9d. Human peripheral blood mononuclear cells (PBMC) were incubated with the indicated concentrations of ProPAgens 4d (left) and 9d (right) for 18 hr. TCR Vγ9/Vδ2⁺ T cells were then assessed for the upregulation of cell surface markers, CD69 and CD25, as a readout to the activation of Vγ9/Vδ2⁺ T cells. $EC_{50}$ for both ProPAgens is ca. 8 pM (picomolar).

Figure 8A:
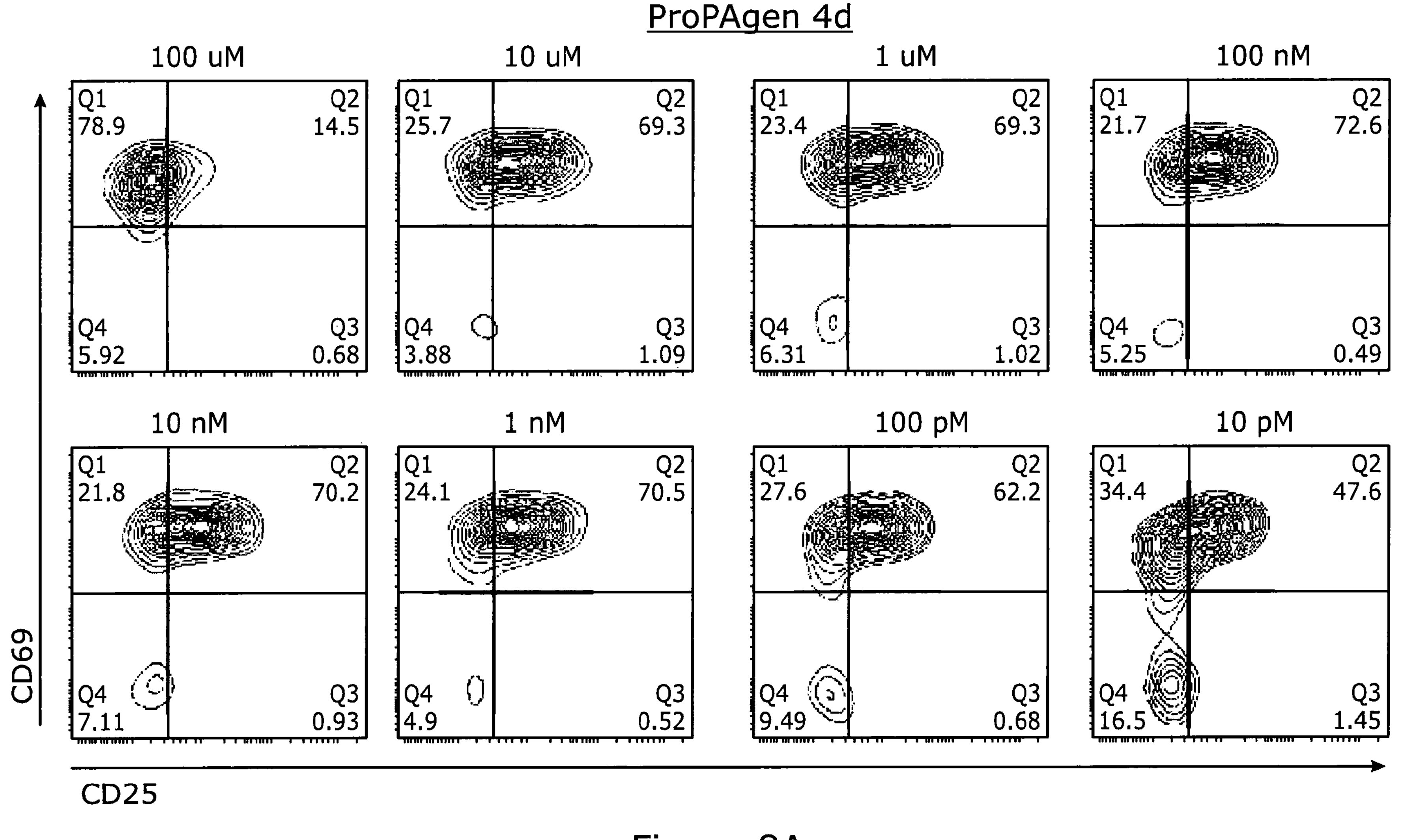
Figure 8B:
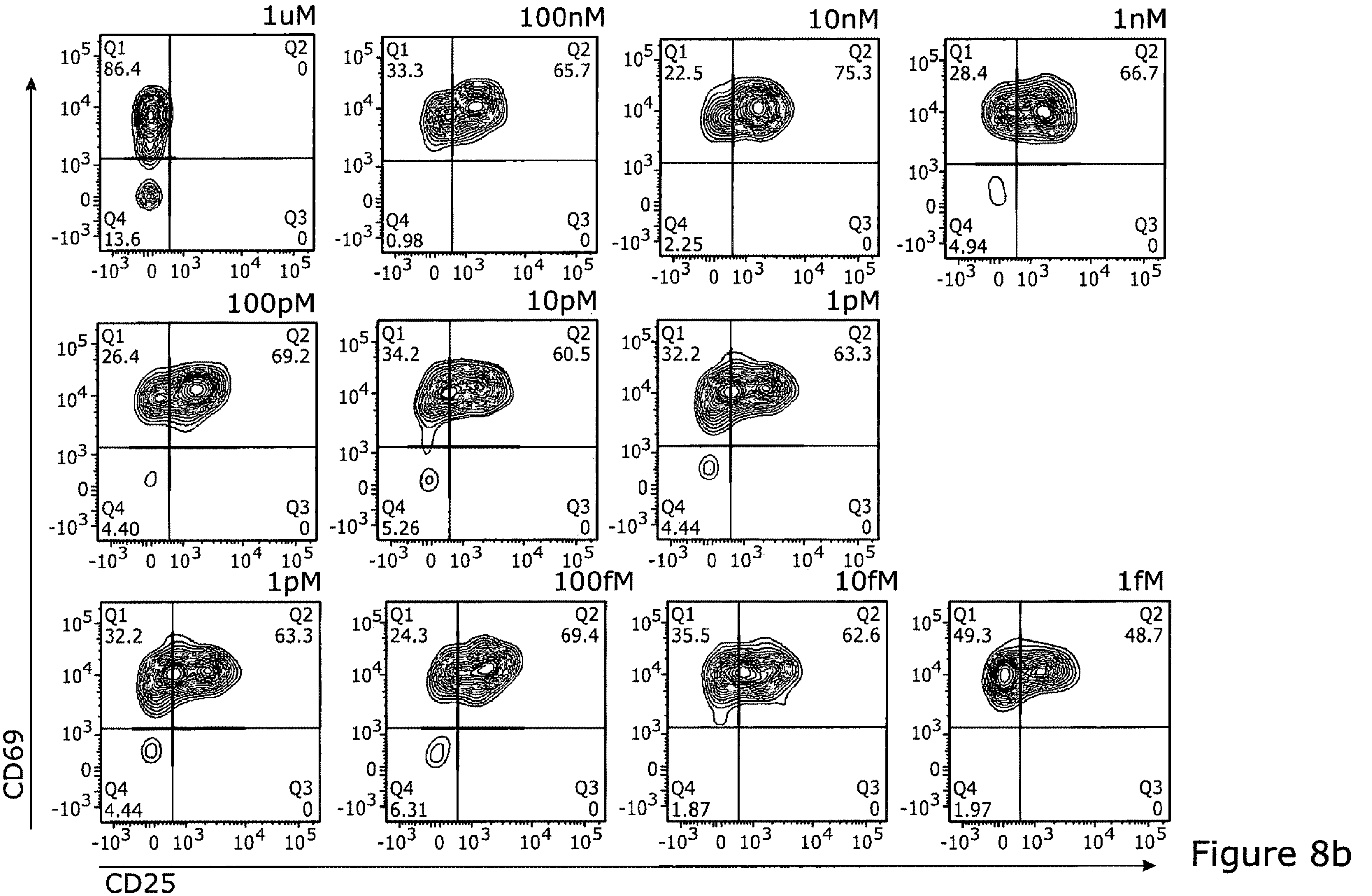
Figure 8C:
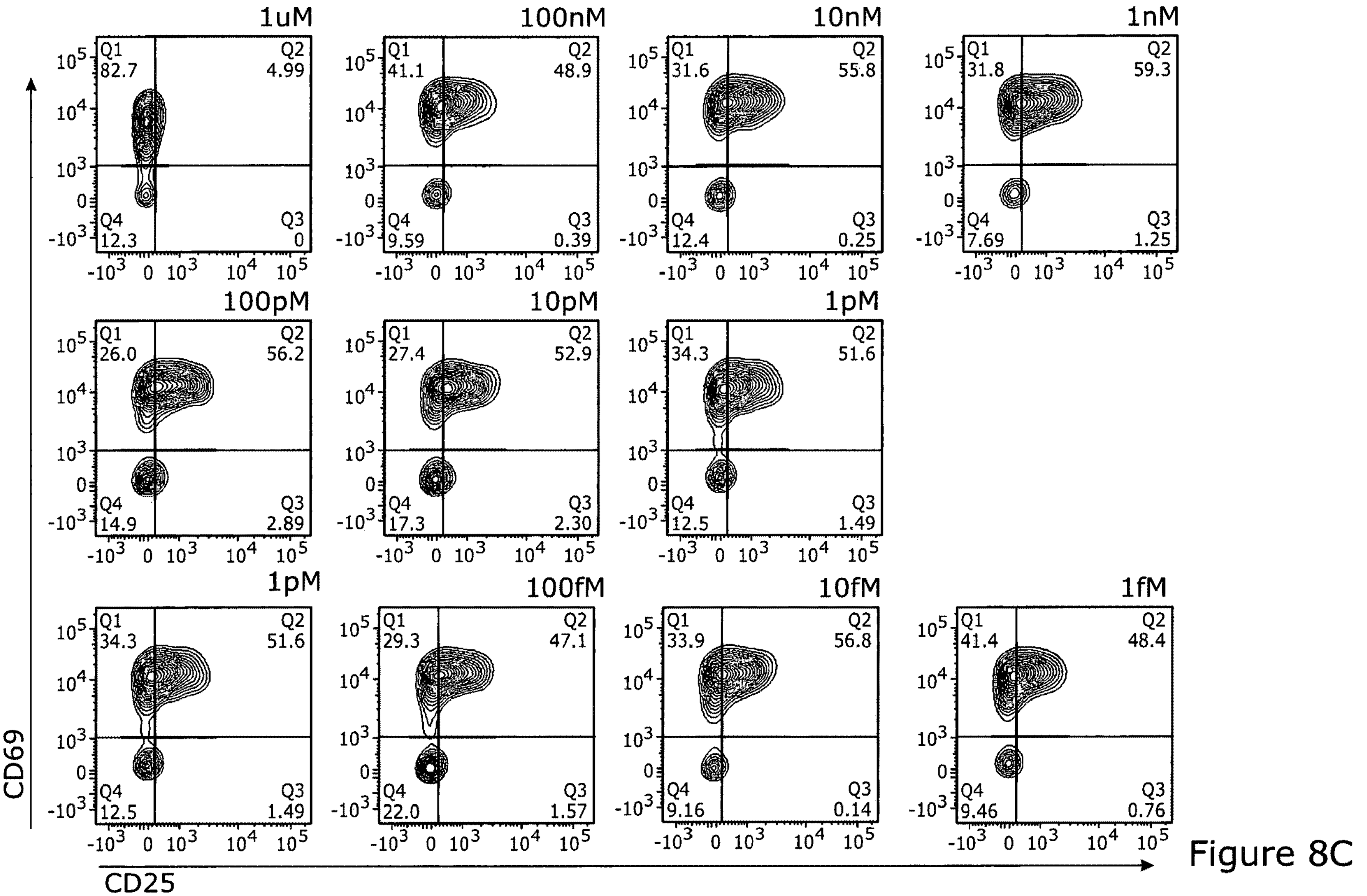

FIG. 8. FACS data showing the activation of human Vγ9/Vδ2⁺ T cells by the HMBP phosphonate ProPAgen 4d in a dose-dependent manner. Human peripheral blood mononuclear cells (PBMC) were incubated with the indicated concentrations of ProPAgens 4d for 18 h (FIG. 8A) or 20 h (FIGS. 8B and 8C). For 20 h incubations, data was collected and analysed individually from two separate donors: Donor (1) results shown in FIG. 8B, Donor (2) results shown in FIG. 8C. TCR Vγ9/Vδ2⁺ T cells were then assessed for the upregulation of cell surface markers, CD69 and CD25, as a readout to the activation of Vγ9/Vδ2⁺ T cells. A quantification of this is given in FIG. 7.

Figure 9A:
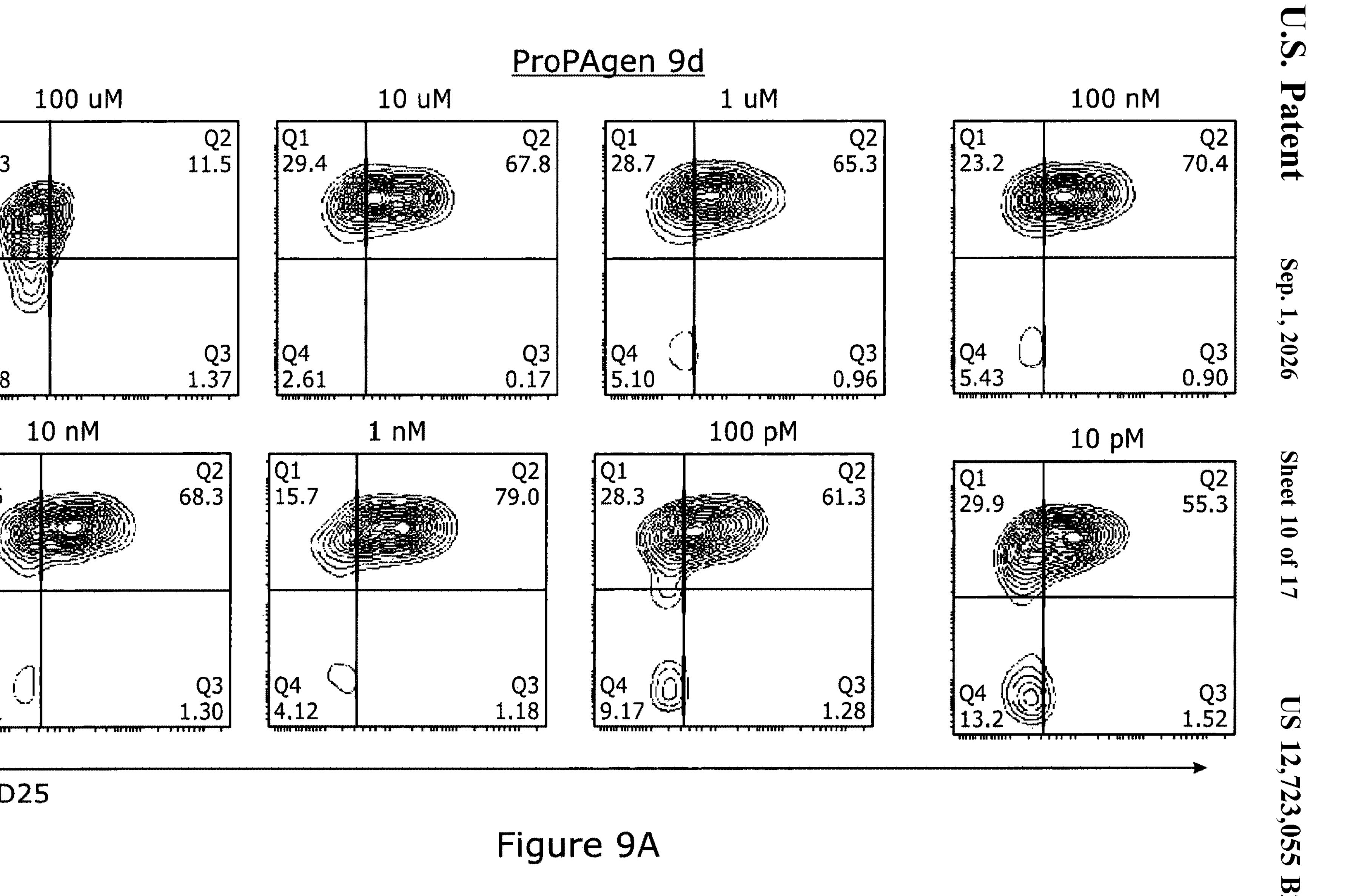
Figure 9B:
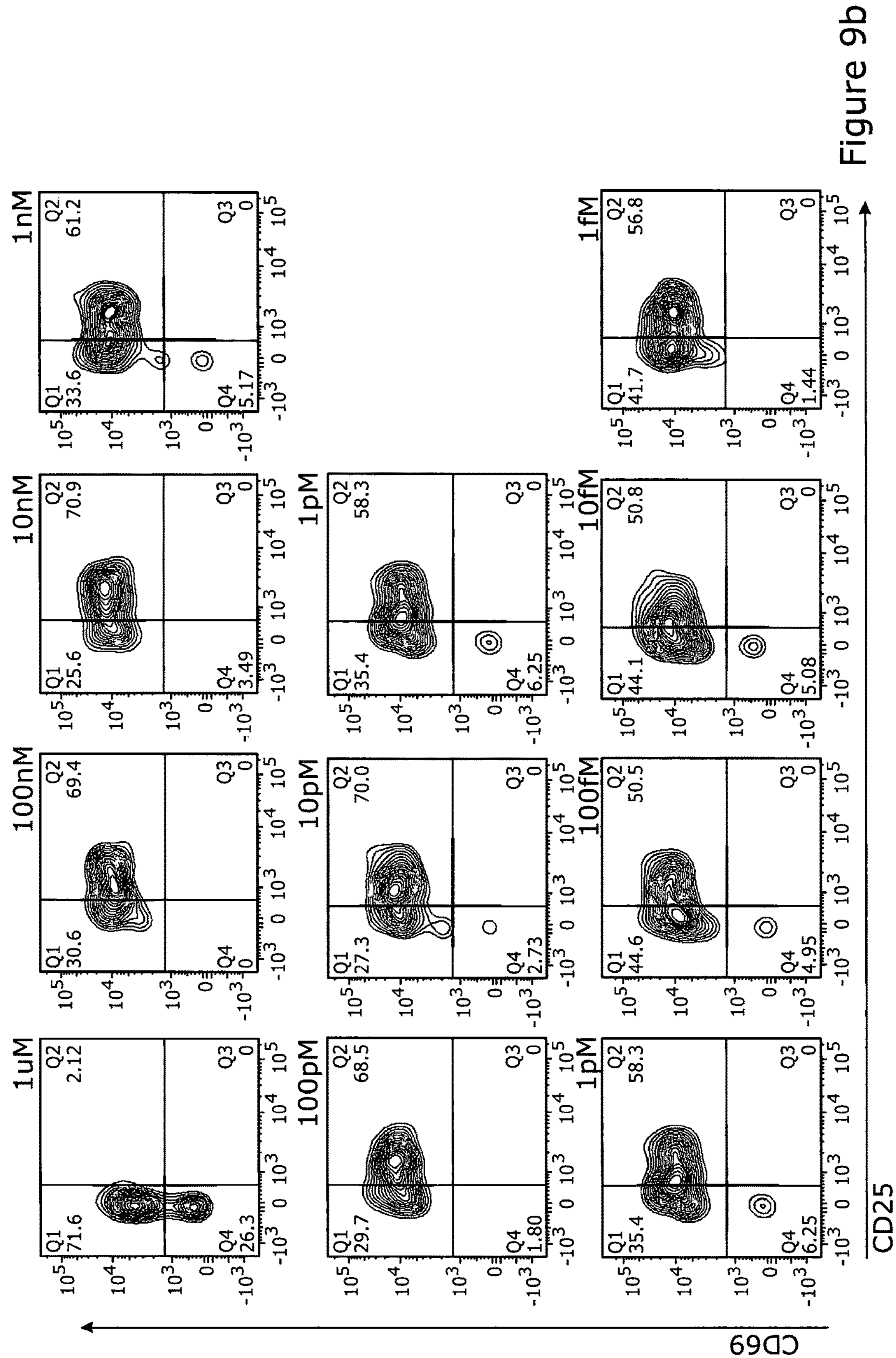
Figure 9C:
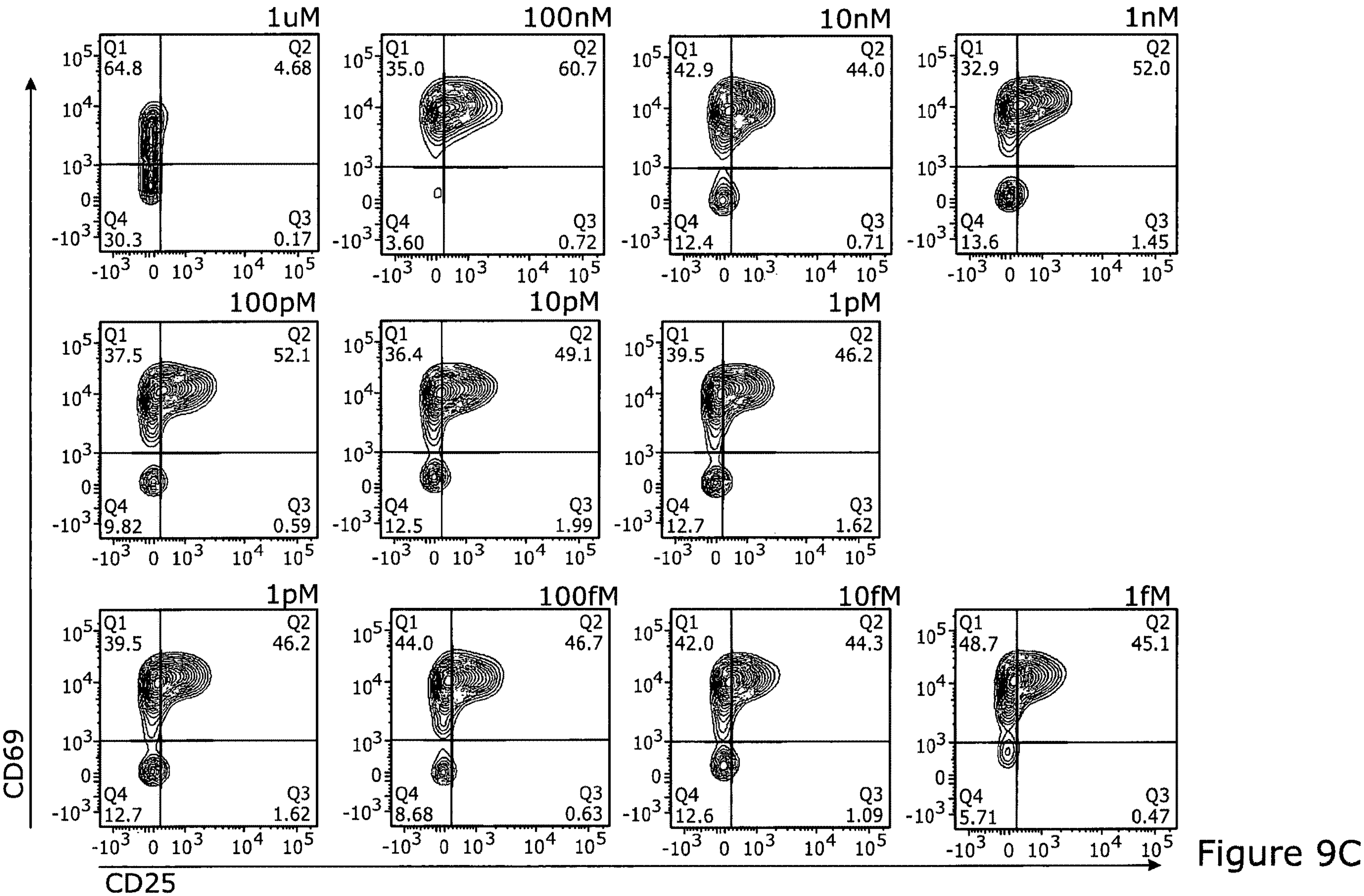

FIG. 9. FACS data showing the activation of human Vγ9/Vδ2⁺ T cells by the HMBP phosphonate ProPAgen 9d in a dose-dependent manner. Human peripheral blood mononuclear cells (PBMC) were incubated with the indicated concentrations of ProPAgens 9d for 18 h (FIG. 9A) or 20 h (FIGS. 9B and 9C). For 20 h incubations, data was collected and analysed individually from two separate donors: Donor (1) results shown in FIG. 9B, Donor (2) results shown in FIG. 9C. TCR Vγ9/Vδ2⁺ T cells were then assessed for the upregulation of cell surface markers, CD69 and CD25, as a readout to the activation of Vγ9/Vδ2⁺ T cells. A quantification of this is given in FIG. 7.

Figure 10A:
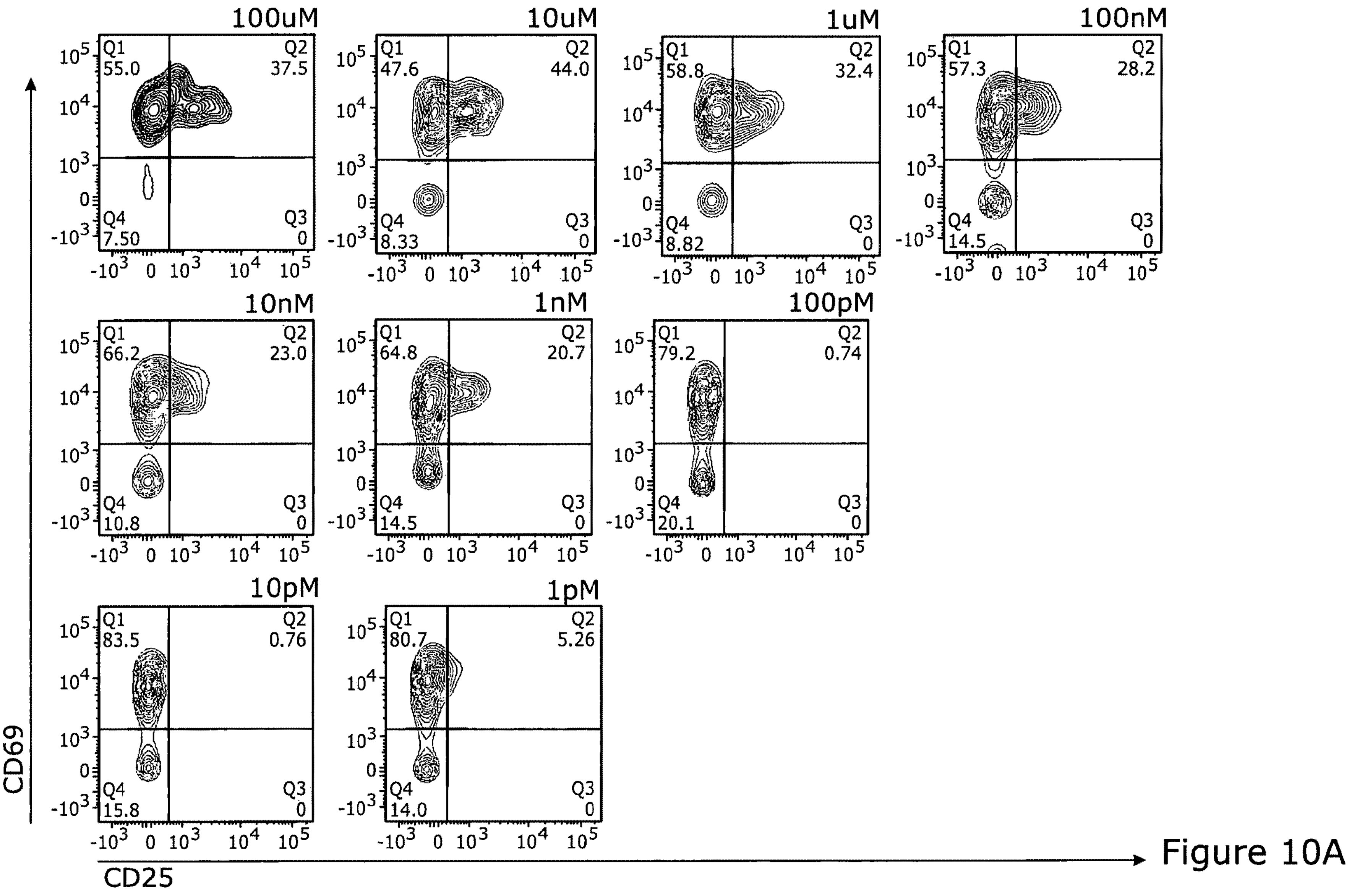
Figure 10B:
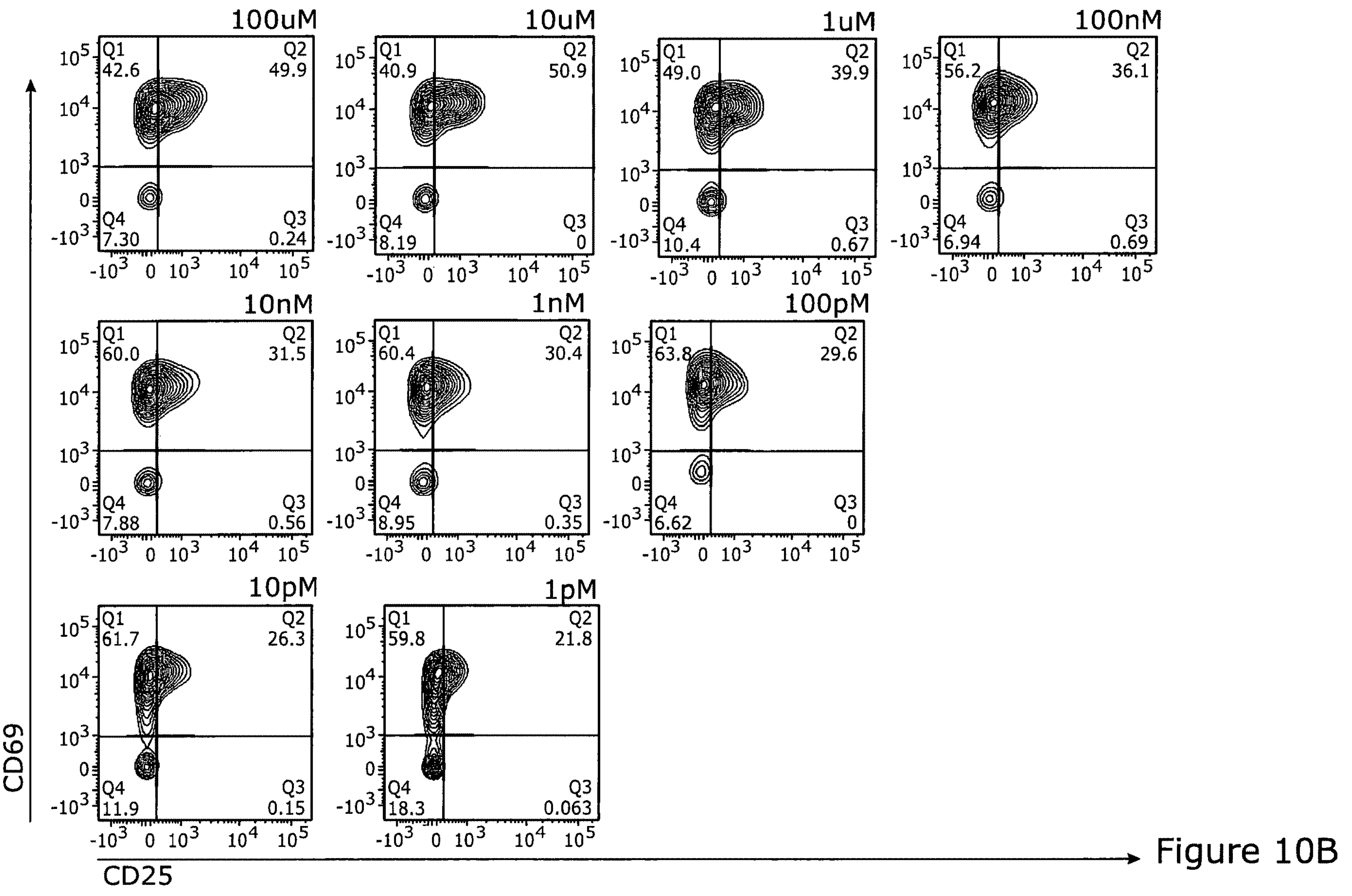

FIG. 10. FACS data showing the activation of human Vγ9/Vδ2⁺ T cells by HMBPP in a dose-dependent manner. Human peripheral blood mononuclear cells (PBMC) were incubated with the indicated concentrations of HMBPP for 20 h. Data was collected and analysed individually from two separate donors: Donor (1) results shown in FIG. 10A, Donor (2) results shown in FIG. 10B. TCR Vγ9/Vδ2⁺ T cells were then assessed for the upregulation of cell surface markers, CD69 and CD25, as a readout to the activation of Vγ9/Vδ2⁺ T cells.

Figure 11A:
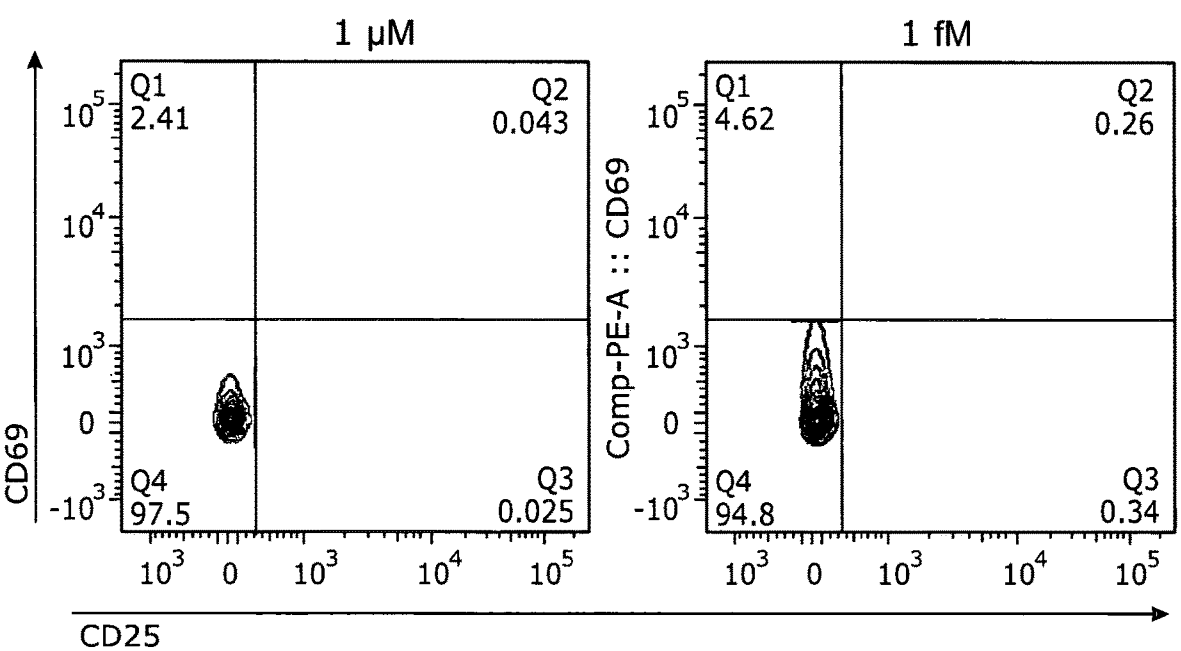
Figure 11B:
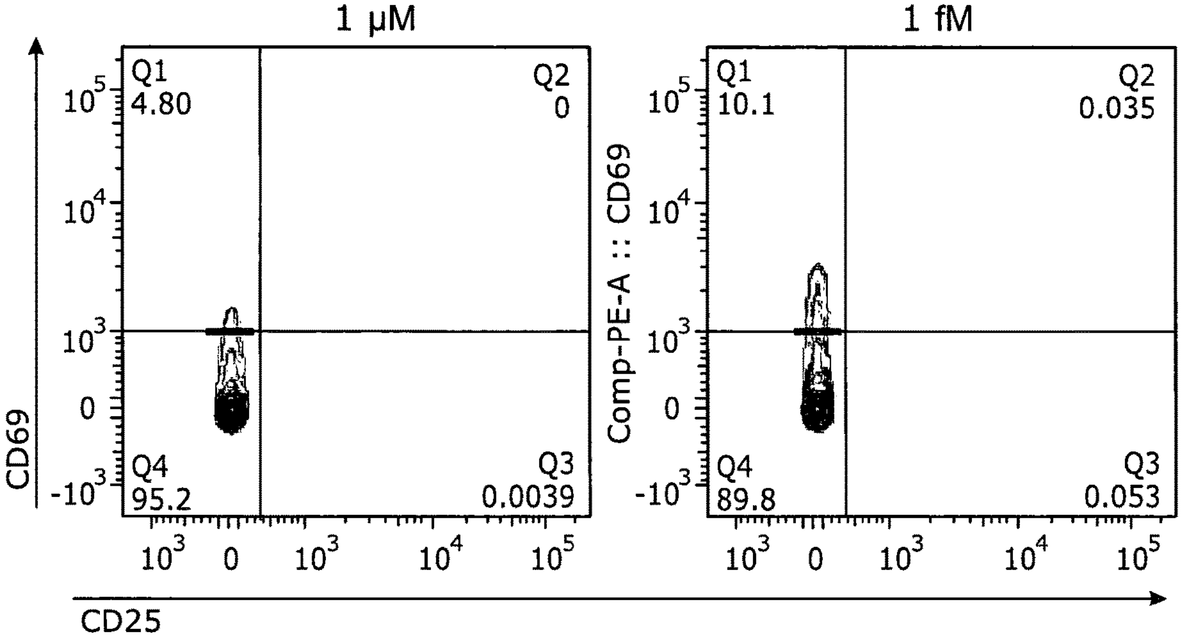

FIG. 11. FACS data showing a lack of activation of human CD8+ T cells by the HMBP phosphonate ProPAgen 4d. Human PBMCs were incubated with the indicated concentrations of ProPAgen 4d for 20 h. TCR CD8⁺ T cells were then assessed for the upregulation of cell surface markers, CD69 and CD25, as a readout of the activation of CD8⁺ T cells. Data was collected and analysed individually from two separate donors: Donor (1) results shown in FIG. 11A, Donor (2) results shown in FIG. 11B.

Figure 12A:
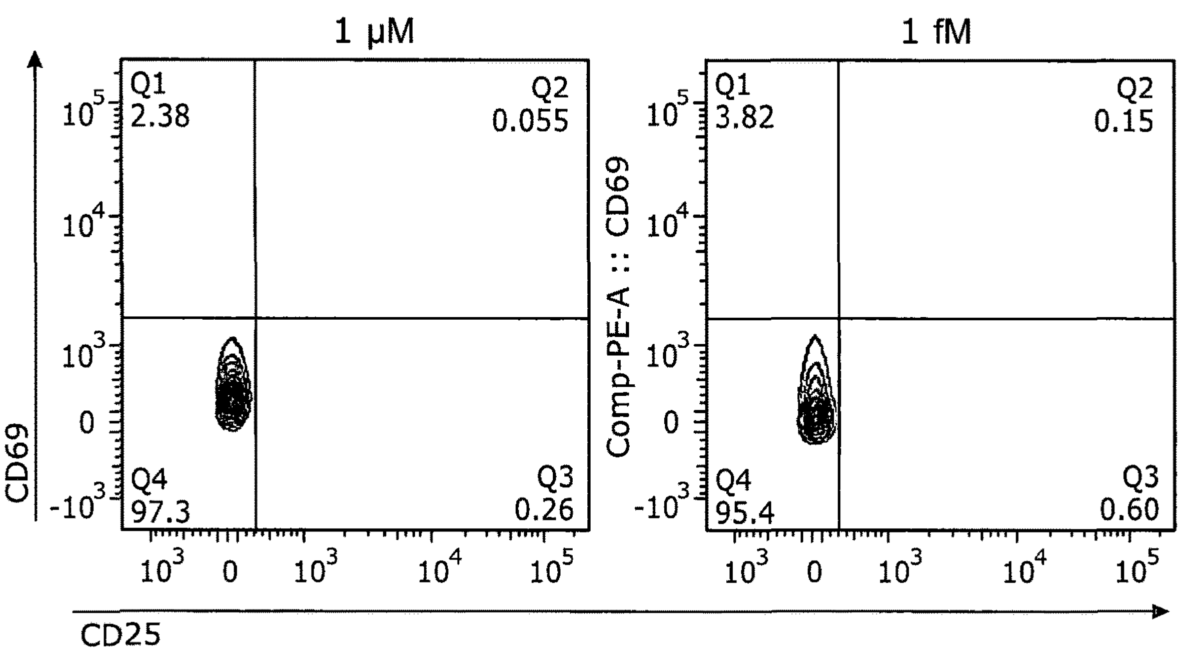
Figure 12B:
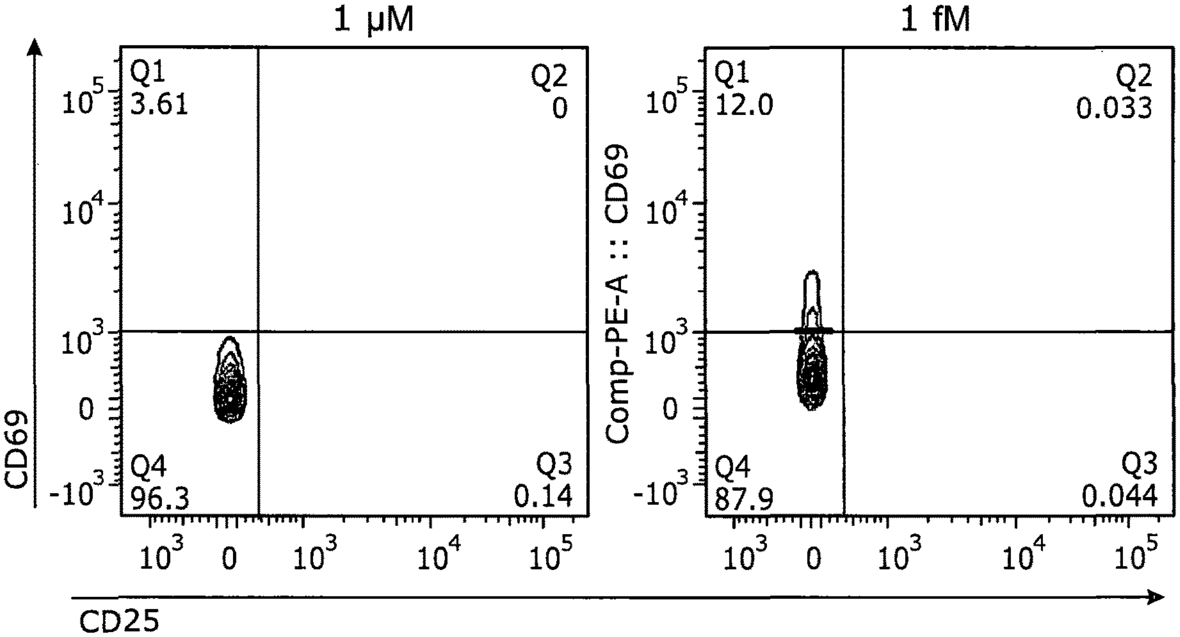

FIG. 12. FACS data showing a lack of activation of human CD8+ T cells by the HMBP phosphonate ProPAgen 9d. Human PBMCs were incubated with the indicated concentrations of ProPAgen 9d for 20 h. TCR CD8⁺ T cells were then assessed for the upregulation of cell surface markers, CD69 and CD25, as a readout of the activation of CD8⁺ T cells. Data was collected and analysed individually from two separate donors: Donor (1) results shown in FIG. 12A, Donor (2) results shown in FIG. 12B.

Figure 13:
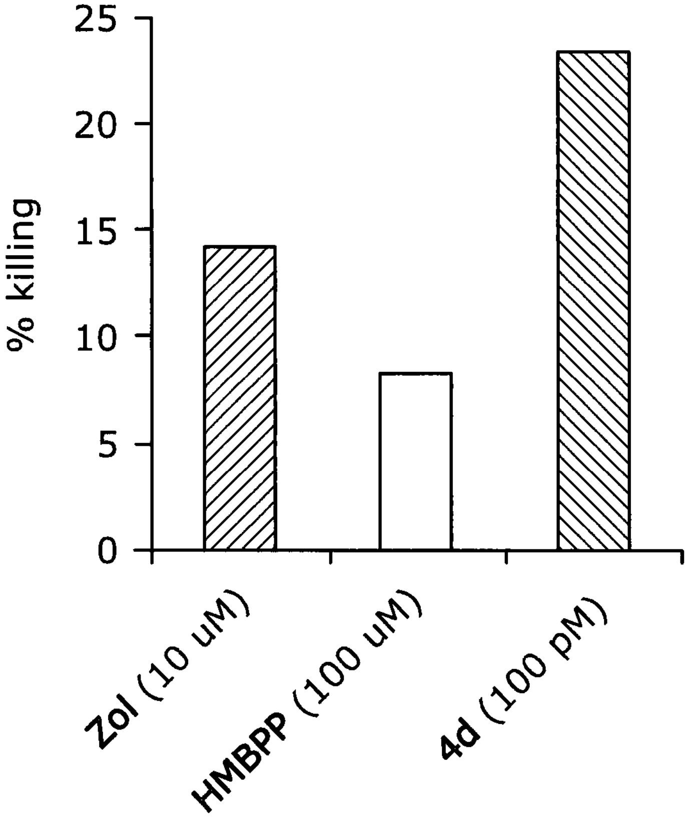

FIG. 13. Cytotoxocity Assay showing potent lysis of bladder cancer cells following incubation with the HMBP phosphonate ProPAgen 4d. ProPAgen 4d mediates the specific lysis of T24 bladder cancer cells by Vγ9/Vδ2 T-cells. Human T24 urinary bladder carcinoma cell lines (target) were incubated for 4 hours with 10 μM zoledronate, 100 pM of HMBPP or 100 pM of ProPAgen 4d, before being washed five-times in medium and co-cultured with previously expanded Vγ9Vδ2 T cells in an effector target ratio of 10:1 for 18 hours.

DETAILED DESCRIPTION

Materials and Methods

All reagents and solvents were of general purpose or analytical grade and were purchased from Sigma-Aldrich Ltd., Fisher Scientific, Fluorochem or Acros. $^{31}P$, $^{1}H$ and $^{13}C$ NMR data were recorded on a Bruker Avance DPX500 spectrometer operating at 202, 500 and 125 MHz. Chemical shifts (δ) are quoted in ppm, and J values are quoted in Hz. In reporting spectral data, the following abbreviations were used: s (singlet), d (doublet), t (triplet), q (quartet), dd (doublet of doublets), td (triplet of doublets), and m (multiplet). All of the reactions were carried out under nitrogen atmosphere and were monitored with analytical thin layer chromatography (TLC) on pre-coated silica plates (kiesel gel 60 F254, BDH). Compounds were visualized by illumination under UV light (254 nm) or by the use of $KMnO_4$ stain followed by heating. Flash column chromatography was performed with silica gel 60 (230-400 mesh) (Merck). Mass spectra (HRMS) were determined as a service by the School of Chemistry at Cardiff University.

Example 1: Synthesis of Aryloxy Phospharamidate ProPAgens of HMBP Methylphosphonates Compounds of general formula (VI) in which R4 and R5 each represent H were prepared by a synthetic approach that employed Grubbs olefin metathesis[7]. The synthesis of ProPAgens 4a-d, which is summarised schematically in FIG. 4(A), was achieved by treating the commercially available diethyl 3-butenylphosphonate (1) with Bromotrimethylsilane (TMSBr) at room temperature to remove the ethoxy groups[8]. This was followed by chlorination reaction using oxalyl chloride in the presence of a catalytic amount of DMF. The product of this reaction, 2, was subsequently treated phenol in the presence of triethylamine and then with the appropriate amino acid ester to yield phosphonamidates 3a-d in moderate yields (38-61%). Subsequently, these compounds underwent Grubbs olefin metathesis with 2-methyl-2-propenol employing Hoveyda-Grubbs second generation catalyst in the presence of 1,4-benzoquinone. This gave ProPAgens 4a-d in good yields (57-64%)[9].

L-alanine was used as the amino acid of choice in the synthesis of ProPAgens 4a-d since it has historically shown the optimum biological activity, while the phenol motif was chosen for the aryloxy masking group as it has been used successfully in the discovery of two FDA-approved drugs; sofosbuvir and tenofovir alafenamide. Four different ester motifs were chosen in the synthesis of the ProPAgens—4a: methyl (Me); 4b: isopropyl (iPr); 4c: tert-butyl (tBu); and 4d: benzyl (Bn), because these show varying biological activities that vary from lowest activity (tBu) to highest activity (Bn)[6].

Further details of the above syntheses can be found in the appendix.

Example 2: Synthesis of Aryloxy Phospharamidate ProPAgens of HMBP Difluoromethylphosphonate Compounds of general formula (VI) in which R4 and R5 each represent F were also prepared using a synthetic approach that employed Grubbs olefin metathesis[7]. The synthesis of ProPAgens 9a-d, which is summarised schematically in FIG. 4(B), was achieved by first reacting the commercially available diethyl (bromodifluoromethyl)phosphonate (5) with allyl bromide in the presence of zinc and copper bromide in DMF as reported[10]. The generated compound, 6, was subsequently chlorinated and then treated with phenol and the appropriate amino acid ester to yield phosphoramidates 8a-d in good yields (24-46%) as described for the synthesis of compounds 3a-d. Subsequently, these phosphonamidates were treated with 2-methyl-2-propenol in the presence of 1,4-benzoquinone and Hoveyda-Grubbs second generation catalyst[9]. The final ProPAgens 9a-d were generated in good yield (58-69%). L-alanine was used as the amino acid of choice in the synthesis of these prodrugs since it has historically shown the optimum biological activity, while the phenol motif was chosen as it has been used successfully in the discovery of two FDA-approved drugs; sofosbuvir and tenofovir alafenamide.

As for ProPAgens 4a-d, L-alanine was used as the amino acid of choice in the synthesis of ProPAgens 9a-d and the phenol motif was chosen for the aryloxy masking group. Again, four different ester motifs were chosen in the synthesis of the ProPAgens—9a: methyl (Me); 9b: isopropyl (iPr); 9c: tert-butyl (tBu); and 4d: benzyl (Bn).

Further details of the above syntheses can be found in the enclosed appendix.

Example 3: Stability Studies of HMBP Methylphosphonates and HMBP Difluoromethylphosphonates As it was a primary objective to address the poor stability previously observed for HMBP phosphate ProPAgens[6], Serum stability studies were carried out upon the completion of the synthesis of the novel compounds in Examples 1 and 2.

ProPAgen 4d with human serum at 37° C. for 12 h and monitored the sample by $^{31}$P-NMR as reported previously[11]. As shown in FIG. 5, ProPAgen 4d had two singlets at dP=33.60 and 34.05 ppm, on the $^{31}$P-NMR corresponding to the two diastereoisomers that arise from the chiral phosphorous center, which is typical of these prodrugs. Following the addition of human serum and monitoring of the sample by $^{31}$P-NMR, there was no degradation observed since no new phosphorous peaks were detected for the period studied (12 h).

A similar stability profile was observed for the difluoromethyl phosphonate ProPAgen 9a (FIG. 6). Together, these data indicate the superior stability of these prodrugs in comparison to the HMBP phosphate ProPAgens that we previously disclosed[6].

Example 4: Activation of Human Vγ9/Vδ2$^+$ T Cells by ProPAgens 4a-d and 9a-d

To demonstrate that the ProPAgens of Examples 1 and 2 retained potent activation of Vγ9/Vδ2 T-cells, peripheral blood mononuclear cells (PBMCs) containing Vγ9/Vδ2 T-cells derived from healthy donors were incubated with increasing concentrations of ProPAgens 4d and 9d (FIGS. 7, 8 and 9).

Peripheral blood γδ T-cells lack appreciable levels of surface CD69 or CD25 under steady state conditions, but upon T-cell receptor (TCR) stimulation upregulate both T-cell activation markers within 72 hours. PAg responsive Vγ9/Vδ2 T-cells were then distinguished by TCR Vγ9 and Vδ2 expression and assessed for the upregulation CD69 and CD25.

As shown in FIGS. 7, 8, and 9, HMBP phosphonate ProPAgens 4d and 9d, as representatives of these classes of prodrugs, exhibited potent Vγ9/Vδ2 T-cells activation that is far superior to that reported for HMBP phosphate ProPAgens[6].

Example 5 (Comparative): Activation of Human Vγ9/Vδ2$^+$ T Cells by HMBPP

To demonstrate the enhanced Vγ9/Vδ2 T-cell activation potency of the ProPAgens of Examples 1 and 2, peripheral blood mononuclear cells (PBMCs) containing Vγ9/Vδ2

T-cells derived from healthy donors were incubated for comparative purposes with increasing concentrations of HMBPP (FIG. 10).

As is evident upon comparison of FIGS. 8 and 9 with FIG. 10, the T-cell activation potency of HMBPP is inferior to that activation potency of ProPAgens 4d and 9d.

Example 6: Lack of Activation of Human CD8+ T Cells by ProPAgens 4a-d and 9a-d

To demonstrate that the ProPAgens of Examples 1 and 2 are Vγ9/Vδ2 T cell—specific activators, PBMCs containing CD8+ T-cells derived from donors were incubated with increasing concentrations of ProPAgens 4d and 9d (FIGS. 11 and 12).

Like peripheral blood γδ T-cells, peripheral blood CD8+ T-cells lack appreciable levels of surface CD69 or CD25 under steady state conditions, but upon T-cell receptor (TCR) stimulation upregulate both T-cell activation markers within 72 hours. PAg responsive CD8 T-cells were then distinguished by TCR CD8 expression and assessed for the upregulation CD69 and CD25.

As shown in FIGS. 11 and 12, HMBP phosphonate PropAgens 4d and 9d, as representatives of these classes of prodrugs, did not exhibit activation of CD8+ T cells, even upon incubation at a concentration of 1 μM, i.e. approx. 100,000 times greater than the Vγ9/Vδ2 T-cell activation $EC_{50}$ values calculated for both ProPAgens.

Example 7: Lysis of T24 Bladder Cancer Cells by Vγ9/Vδ2 T-Cells is Mediated and Enhanced by ProPAgens 4a-d and 9a-d As a further proof of principle, and to demonstrate that the superior Vγ9/Vδ2$^+$ T cell activation efficacy of ProPAgens of Examples 1 and 2 shown above does translate into a beneficial therapeutic effect, the specific lysis of cancer cells by Vγ9/Vδ2 T-cells was compared following incubation of human T24 urinary bladder carcinoma cell lines for 4 hours with 10 μM zoledronate, 100 μM of HMBPP or 100 pM of ProPAgen 4d.

Further details of this in vitro cytotoxicity assay can be found in the enclosed appendix.

As shown in FIG. 13, incubation with HMBP phosphonate PropAgen 4d resulted in a significant enhancement in T24 bladder cancer lysis in comparison not only to that observed upon incubation with zoledronate but also, surprisingly, compared to that observed upon incubation with HMBPP.

Summary

We report the synthesis of novel methyl and difluoromethyl phosphonate ProPAgens. These ProPAgens exhibited superior serum stability compared to their phosphate ProPAgens derivatives, which were previously reported[6]. These prodrugs were shown not only to be specific activators of Vγ9/Vδ2 T-cells, but also to be far more potent activators of Vγ9/Vδ2 T-cells than the previously reported HMBP phosphate ProPAgens. This increase in Vγ9/Vδ2 T-cells activation efficacy was also shown to translate to highly potent lysis of cancer cells in vitro.

The combination of high, specificity, serum stability and potency profiles of these new phosphonate ProPAgens makes them suitable for development as new immunotherapeutics for treating a variety of conditions, including proliferative diseases such as cancer, osteoporosis and/or various infections such as tuberculosis, leprosy, typhoid, malaria, and toxoplasmosis.

APPENDIX: SYNTHESIS AND EVALUATION OF PROPAGEN COMPOUNDS 4A-D AND 9A-D

But-3-en-1-ylphosphonic dichloride (2). Trimethylsilylbromide (13.72 mL, 104.06 mmol, 10 eq.) was slowly added over 30 min to diethylbut-3-en-1-yl phosphonate 1 (2 g, 10.40 mmol, 1 eq.) in CH2Cl2 (50 mL) under nitrogen at room temperature. The mixture was stirred for 2 h followed by the removal of volatiles under reduced pressure to obtain a yellow liquid $\delta_P$ NMR (202 MHz, $CDCl_3$): 24.70. The was then dissolved in 50 mL $CH_2Cl_2$ and two drops of dry DMF were added and the mixture was cooled to 0° C. Oxalyl chloride (2.68 mL, 31.20 mmol, 3 eq.) was then added dropwise and the reaction mixture was allowed to warm to room temperature and stirred for 18 h. The volatiles were evaporated and additional $CH_2Cl_2$ (10 mL) was evaporated three more times to give the crude product (1.79 g, 100%) as a brown liquid which was used in the next step without further purification. $\delta_P$ NMR (202 MHz, $CDCl_3$): 49.66.

General procedure 1. Synthesis of allylphosphonoamidates 3a-d. The crude product but-3-en-1-ylphosphonic dichloride (2) was dissolved in 5 mL $CH_2Cl_2$ and added dropwise to a solution of phenol (1 eq.), dry $Et_3N$ (2 eq.) and $CH_2Cl_2$ (10 mL) at −78° C. After stirring at −78° C. for 30 min, the reaction mixture was allowed to warm to room temperature and stirring was continued for another 3 h. Once the reaction is complete as indicated by $^{31}$P NMR [op NMR (202 MHz, $CDCl_3$): ~39.93], the mixture was filtered, and the volatiles were removed under reduced pressure, washed twice with $Et_2O$, which was subsequently removed under reduced pressure to give a crude oil. This product was then dissolved in $CH_2Cl_2$ (10 mL) and was added dropwise over 15 min to a stirring mixture of L-alanine ester hydrogen chloride (1 eq.) and dry $Et_3N$ (2 eq.) in dry $CH_2Cl_2$ (10 mL) under nitrogen at −78° C. After stirring at −78° C. for 30 mins, the reaction was allowed to warm to room temperature and was left stirring overnight. The solvents were removed under reduced pressure, and the mixture was filtered and washed with $Et_2O$, which was then removed under reduced pressure to give a crude oil. The final products were then purified by column chromatography (6:4 Hex/EtOAc) as colorless oils.

Methyl (but-3-en-1-yl(phenoxy)phosphoryl)-L-alaninate (3a). Synthesised following general procedure 1 using phenol (0.210 g, 2.23 mmol, 1 eq.) and L-alanine methyl ester hydrogen chloride (0.373 g, 2.23 mmol, 1 eq.) to give product 3a (0.248 g, 38%) as a colorless oil. $\delta_P$ NMR (202 MHz, $CDCl_3$): 30.88, 31.22. $\delta_H$ NMR (500 MHz, $CDCl_3$): 7.30 (m, 2H, Ar), 7.10 (m, 3H, Ar), 5.82 (m, 1H, $CH_2$=CH), 5.00 (m, 2H, $CH_2$=CH), 4.11-3.86 (m, 1H, CH—NH), 3.60 (d, J=6.6 Hz, 3H, $OCH_3$), 3.18 (m, 1H, NH), 2.48-2.27 (m, 2H, =CH—$CH_2$), 1.92 (m, 2H, $CH_2$—P), 1.21 (2 d, J=7.1 Hz, 3H, CH—$CH_3$). $\delta_C$ NMR (126 MHz, $CDCl_3$): 174.68 (d, J=6.3 Hz, C=O), 174.38 (d, J=5.1 Hz, C=O), 150.72 (d, J=9.1 Hz), 150.51 (d, J=9.4 Hz), 129.78, 124.78 (d, J=5.5 Hz, CH=$CH_2$), 120.86 (d, J=4.6 Hz, C—Ar), 120.71 (d, J=4.7 Hz), 115.56, 52.52 (d, J=3.1 Hz, $CH_3$—O), 49.58 (d, J=14.7 Hz, CH—NH), 27.88 (d, J=130.9 Hz, $CH_2$—P) 27.60 (d, J=131.6 Hz, $CH_2$—P), 26.59 (d, J=4.1 Hz, $CH_2$—$CH_2$—P), 21.68 (2 d, J=4.3 Hz, $CHCH_3$).

Isopropyl (but-3-en-1-yl(phenoxy)phosphoryl)-L-alaninate (3b). Synthesised following general procedure 1 using phenol (0.210 g, 2.23 mmol, 1 eq.) and L-alanine isopropyl ester hydrogen chloride (0.373 g, 2.23 mmol, 1 eq.) to give product 3b (0.348 g, 48%) as a colorless oil. $\delta_P$ NMR (202 MHz, $CDCl_3$): 30.93, 31.24. $\delta_H$ NMR (500 MHz, $CDCl_3$): 7.30 (m, 2H, Ar), 7.21 (m, 3H, Ar), 5.81 (m, 1H, $CH_2$=CH), 5.11 (m, 2H, $CH_2$=CH), 4.96 (m, 1H, CH-iPr), 4.04-3.94 (m, 1H, CH—NH), 3.21 (m, 1H, NH), 2.45 (m, 2H, =CH—$CH_2$), 2.02-1.88 (m, 2H, $CH_2$—P), 1.29-1.18 (m, 9H, $CH_3$—CH—NH, CH-iPr). $\delta_C$ NMR (126 MHz, $CDCl_3$): 173.67 (d, J=6.3 Hz, C=O), 150.74 (d, J=9.1 Hz), 129.76 (d, J=6.7 Hz), 124.73 (d, J=5.0 Hz), 120.86 (d, J=4.6 Hz), 120.69 (d, J=4.6 Hz), 115.50, 69.23 (d, J=5.6 Hz, CHiPr), 49.75 (d, J=9.5 Hz, CH—NH), 27.89 (d, J=130.9 Hz, $CH_2$—P), 27.54 (d, J=131.4 Hz, $CH_2$—P), 26.74 (d, J=4.3 Hz, $CH_2$—$CH_2$—P), 26.57 (d, J=4.0 Hz, $CH_2$—$CH_2$—P), 21.58 (2 d, J=4.4 Hz, $CHCH_3$).

tert-Butyl (but-3-en-1-yl(phenoxy)phosphoryl)-L-alaninate (3c). Synthesised following general procedure 1 using phenol (0.210 g, 2.23 mmol, 1 eq.) and L-alanine tert-Butyl ester hydrogen chloride (0.405 g, 2.23 mmol, 1 eq.) to give product 3c (0.461 g, 61%) as a colorless oil. $\delta_P$ NMR (202 MHz, $CDCl_3$): 30.95, 31.21. $\delta_H$ NMR (500 MHz, $CDCl_3$): 7.32 (m, 2H, Ar), 7.20 (m, 3H, Ar), 5.87 (m, 1H, $CH_2$=CH), 5.12 (m, 2H, $CH_2$=CH), 4.00-3.86 (m, 1H, CH—NH), 3.26 (m, 1H, NH), 2.45 (m, 2H, =CH—$CH_2$), 2.04-1.85 (m, 2H, P—$CH_2$), 1.42 (s, 9H, tBu-H), 1.22 (2 d, J=7.2 Hz, 3H, CH—$CH_3$). $\delta_C$ NMR (126 MHz, $CDCl_3$): 173.13 (d, J=5.5 Hz, C=O), 150.77 (d, J=9.2 Hz), 137.43 (d, J=7.1 Hz), 137.32 (d, J=7.6 Hz), 129.76 (d, J=6.2 Hz), 124.71 (d, J=4.0 Hz), 120.88 (d, J=4.6 Hz), 120.72 (d, J=4.7 Hz), 115.47, 81.99 (d, J=8.2 Hz), 60.54, 50.18 (d, J=4.0 Hz, CH—NH), 28.05, 27.91 (d, J=131.6 Hz, $CH_2$—P), 27.20 (d, J=130.2 Hz, $CH_2$—P), 21.82 (2 d, J=4.2 Hz, $CHCH_3$).

Benzyl (but-3-en-1-yl(phenoxy)phosphoryl)-L-alaninate (3d). Synthesised following general procedure 1 using phenol (0.210 g, 2.23 mmol, 1 eq.) and L-alanine benzyl ester hydrogen chloride (0.405 g, 2.23 mmol, 1 eq.) to give product 3d (0.461 g, 55%) as a colorless oil. $\delta_P$ NMR (202 MHz, $CDCl_3$): 30.85, 31.21. $\delta_H$ NMR (500 MHz, $CDCl_3$): 7.38-7.27 (m, 7H, Ar), 7.21-7.18 (m, 2H, Ar), 7.16-7.09 (m, 1H, Ar), 5.85 (m, 1H, $CH_2$=CH), 5.04 (m, 4H, $CH_2$=CH, —$OCH_2$), 4.28-4.03 (m, 1H, CH—NH), 3.24 (m, 1H, NH), 2.56-2.34 (m, 2H, =CH—$CH_2$), 2.08-1.82 (m, 2H, P—$CH_2$), 1.24 (2 d, J=7.1 Hz, 3H, CH—$CH_3$). $\delta_C$ NMR (126 MHz, $CDCl_3$): 173.74 (d, J=5.2 Hz, C=O), 150.70 (d, J=9.1 Hz), 137.35, 135.40 (d, J=6.7 Hz), 129.79 (d, J=6.1 Hz), 128.79 (d, J=2.8 Hz), 128.64 (d, J=6.4 Hz), 128.33, 120.86 (d, J=4.6 Hz), 120.68 (d, J=4.7 Hz), 115.55, 67.31 (d, J=3.0 Hz, $CH_2$—O), 49.72 (d, J=11.1 Hz, CH—NH), 27.88 (d, J=130.7 Hz, $CH_2$—P), 27.57 (d, J=131.3 Hz, $CH_2$—P), 26.74 (d, J=4.3 Hz, $CH_2$—$CH_2$—P), 26.57 (d, J=4.1 Hz, $CH_2$—$CH_2$—P), 21.70 (2 d, J=4.4 Hz, $CHCH_3$).

General procedure 2. Synthesis of phosphonoamidates 4a-d through Hoveyda-Grubbs cross metathesis. To a solution of allylphosphonoamidates 3a-d (1 eq.) and 2-methyl-2-propen-1-ol (85 μL, 1 mmol, 2 eq.), 1,4-benzoquinone (5.40 mg, 10 mol %) in dry DCM (10 mL) was added Hoveyda-Grubbs catalyst $2^{nd}$ generation (23.5 mg, 0.038 mmol, 7.5 mol %). The catalyst was added in three equal portions of 2.5 mol % (7.8 mg, 0.013 mmol) at t=0, 2 and 4 h over the course of the reaction. The solution was then heated to reflux at 45° C. under nitrogen atmosphere for 18 h. After cooling to room temperature, a scoop of activated carbon was added, and the mixture stirred for another 2 hr then filtered through a Celite pad. Volatiles were evaporated and the residue was purified by extensive silica gel column chromatography (Hexane/EtOAc, 7:3 to 0:10) to give 4a-d as colorless oils.

Methyl (((E)-5-hydroxy-4-methylpent-3-en-1-yl)(phenoxy)phosphoryl)-L-alaninate (4a). Synthesised following general procedure 2 using 3a (150 mg, 0.5 mmol, 1 eq.) to give 4a (91 mg, 57%) as a colorless oil. $\delta_P$ NMR (202 MHz, $CDCl_3$): 30.89, 31.31. $\delta_H$ NMR (500 MHz, $CDCl_3$): 7.31 (m, 2H, Ar), 7.18 (m, 3H, Ar), 5.48 (m, 1H, =CH), 4.24-3.98 (m, 3H, $CH_2OH$, CH—NH), 3.68 (d, J=7.9 Hz, 3H, $OCH_3$), 3.39-3.18 (m, 1H, NH), 2.55-2.41 (m, 2H, =CH—$CH_2$), 2.12-1.87 (m, 2H, $CH_2$—P), 1.71 (d, J=6.6 Hz, 3H, $CH_3(CH_2)C$=), 1.27 (2×d, J=7.1 Hz, 3H, CH—$CH_3$). $\delta_C$ NMR (126 MHz, $CDCl_3$): 176.71 (d, J=5.9 Hz, C=O), 150.72, 129.81 (d, J=6.9 Hz), 124.81 (d, J=8.6 Hz, CH=$CH_2$), 124.17, 124.04, 120.94, 120.69 (d, J=4.6 Hz), 68.56 (d, J=9.1 Hz, $CH_2$—OH), 52.64 (d, J=3.5 Hz, CHs-0), 49.51 (d, J=4.1 Hz, CH—NH), 28.33 (d, J=129.6 Hz $CH_2$—P), 28.06 (d, J=130.2 Hz, $CH_2$—P), 21.86 (2 d, J=4.9 Hz, $CHCH_3$), 21.00 (d, J=4.8 Hz, $CH_2$—$CH_2$—P), 20.89 (d, J=4.4 Hz, $CH_2$—$CH_2$—P), 13.87. HRMS (ES+, m/z) calcd. for (M+Na)+ $C_{16}H_{24}NO_5NaP$: 364.1290; found: 364.1293.

Isopropyl (((E)-5-hydroxy-4-methylpent-3-en-1-yl)(phenoxy)phosphoryl)-L-alaninate (4b). Synthesised following general procedure 2 using 3b (0.150 g, 0.46 mmol, 1 eq.) to give product 4b (97 mg, 59%) as a colorless oil. $\delta_P$ NMR (202 MHz, $CDCl_3$): 31.11, 31.49. $\delta_H$ NMR (500 MHz, $CDCl_3$): 7.28 (m, 2H, Ar), 7.20 (m, 3H, Ar), 5.46 (m, 1H, =CH), 4.95 (m, 1H, CH-iPr), 4.08-3.79 (m, 3H, $CH_2OH$, CH—NH), 3.47-3.25 (m, 1H, NH), 2.51-2.35 (m, 2H, =CH—$CH_2$), 2.02-1.85 (m, 2H, $CH_2$—P), 1.73-1.56 (d, J=6.0 Hz, 3H, $CH_3(CH_2)C$=), 1.35-1.08 (m, 9H, $CH_3$—CH—NH, CH-iPr). $\delta_C$ NMR (126 MHz, $CDCl_3$): 173.62 (d, J=5.8 Hz, C=O), 150.74 (d, J=9.0 Hz), 136.76, 124.75, 123.95 (d, J=5.4 Hz), 123.84 (d, J=6.9 Hz), 120.90 (d, J=4.5 Hz), 120.67 (d, J=4.6 Hz), 119.83, 115.58, 69.41 (d, J=4.7 Hz, CHiPr) 68.39 (d, J=7.0 Hz, $CH_2$—OH), 49.65, 28.36 (d, J=129.7 Hz, $CH_2$—P), 27.92 (d, J=131.1 Hz, $CH_2$—P), 21.83 (2 d, J=6.2 Hz, $CHCH_3$), 20.90 (d, J=4.4 Hz, $CH_2$—$CH_2$—P), 20.84 (d, J=4.4 Hz, $CH_2$—$CH_2$—P), 13.84. HRMS (ES+, m/z) calcd. for (M+Na)+ $C_{18}H_{28}NO_5NaP$: 392.1603; found: 392.1613.

tert-Butyl (((E)-5-hydroxy-4-methylpent-3-en-1-yl)(phenoxy)phosphoryl)-L-alaninate (4c). Synthesised following general procedure 2 using 3c (0.150 g, 0.44 mmol, 1 eq.) to give product 4c (108 mg, 64%) as a colorless oil. $\delta_P$ NMR (202 MHz, $CDCl_3$): 31.05, 31.42. $\delta_H$ NMR (500 MHz, $CDCl_3$): 7.30 (m, 2H, Ar), 7.17 (m, 3H, Ar), 5.46 (m, 1H, =CH), 4.17-3.78 (m, 3H, $CH_2OH$, CH—NH), 3.41-3.18 (m, 1H, NH), 2.60-2.30 (m, 2H, =CH—$CH_2$), 2.01-1.87 (m, 2H, $CH_2$—P), 1.69 (d, J=6.8 Hz, 3H, $CH_3(CH_2)C$=), 1.42 (s, 9H, tBu), 1.27 (2 d, J=7.9 Hz, 3H, CH—$CH_3$). $\delta_C$ NMR (126 MHz, $CDCl_3$): 173.34 (d, J=6.0 Hz, C=O), 150.79 (d, J=9.0 Hz), 136.81 (d, J=9.6 Hz), 115.59, 82.22 (d, J=5.6 Hz), 68.45 (d, J=10.4 Hz, $CH_2$—OH), 50.07 (d, J=4.5 Hz, CH—NH), 28.01 (d, J=129.7 Hz, $CH_2$—P), 27.26 (d, J=130.4 Hz, $CH_2$—P), 21.98 (d, J=3.8 Hz, $CHCH_3$), 20.97 (d, J=4.7 Hz, $CH_2$—$CH_2$—P), 20.88 (d, J=4.4 Hz, $CH_2$—$CH_2$—P), 13.86 ($CH_3$). HRMS (ES+, m/z) calcd. for (M+Na)+ $C_{19}H_{30}NO_5NaP$: 406.1759; found: 406.1762.

Benzyl ME)-5-hydroxy-4-methylpent-3-en-1-yl)(phenoxy)phosphoryl)-L-alaninate (4d). Synthesised following general procedure 2 using 3d (0.150 g, 0.4 mmol, 1 eq.) to give product 4d (100 mg, 59%) as a colorless oil. $\delta_P$ NMR (202 MHz, $CDCl_3$): 30.90, 31.32, 6H NMR (500 MHz, $CDCl_3$): 7.39-7.28 (m, 7H, Ar), 7.22-7.17 (m, 2H, Ar), 7.12 (m, 1H, Ar), 5.44 (m, 1H, =CH), 5.09 (m, 2H, $OCH_2$), 4.22-3.86 (m, 3H, m, 3H, $CH_2OH$, CH—NH), 3.49-3.17 (m, 1H, NH), 2.64-2.36 (m, 2H, =CH—$CH_2$), 2.04-1.80 (m, 2H, $CH_2$—P), 1.69 (d, J=6.8 Hz, 3H, $CH_3(CH_2)C$=), 1.33 (2 d, J=7.0 Hz, 3H, CH—$CH_3$). $\delta_C$ NMR (126 MHz, $CDCl_3$): 176.76, 129.81 (d, J=7.4 Hz), 128.75 (d, J=14.9 Hz), 128.39, 124.77, 124.15 (d, J=15.0 Hz), 120.93-120.84, 120.67 (d, J=4.7 Hz), 68.57 (d, J=9.6 Hz), 67.42 (d, J=2.9

Hz), 49.65, 28.05 (d, J=129.9 Hz), 21.77 (d, J=4.1 Hz), 20.87 (d, J=4.4 Hz), 13.87. HRMS (ES+, m/z) calcd. for (M+Na)+$C_{22}H_{28}NO_5NaP$: 440.1603; found: 440.1609.

Diethyl (1,1-difluorobut-3-en-1-yl)phosphonate (6).[10] Anhydrous DMF (20 mL) was added to a 250 mL round bottom flask containing activated zinc powder (2.50 g, 38.23 mmol, 1 eq.) under nitrogen. This was followed by slow dropwise addition of diethyl (bromodifluoromethyl)phosphonate (6.80 mL, 38.23 mmol, 1 eq.) and the mixture was stirred for 3 h at room temperature. CuBr (5.48 g, 38.23 mmol, 1 eq.) was added followed by slow dropwise addition of allyl bromide (3.96 mL, 45.87 mmol, 1.2 eq.) to prevent exothermic reaction. After stirring for 40 h, the mixture was filtered and then partitioned between DCM and 10% aqueous $NH_4Cl$. The aqueous phase was extracted three times with DCM. The combined organic phases were dried over anhydrous $MgSO_4$ and concentrated under reduced pressure and the obtained residue was purified by column chromatography using 20% EtOAc in hexane to give 6 (5.41 g, 62%) as a pale-yellow oil. $\delta_P$ NMR (202 MHz, $CDCl_3$): 6.93 (t, J=107.4 Hz). $\delta_H$ NMR (500 MHz, $CDCl_3$): 5.84 (m, 1H, =CH), 5.26 (m, 2H, $CH_2$=), 4.32-4.21 (m, 4H, 2×$OCH_2CH_3$), 2.82 (m, 2H, =CH—$CH_2$), 1.37 (t, J=7.1 Hz, 6H, 2×$OCH_2CH_3$).

(1,1-Difluorobut-3-en-1-yl)phosphonic dichloride (7). Synthesised as described for 2 using 6 (2.5 g, 10.95 mmol, 1 eq.) to give the crude product 7 (2.28 g, 100%) as a brown liquid which was used in the next step without further purification. $\delta_P$ NMR (202 MHz, $CDCl_3$): 31.56 (t, J=138.8 Hz).

Methyl ((1,1-difluorobut-3-en-1-yl)(phenoxy)phosphoryl)-L-alaninate (8a). Synthesised following general procedure 1 using phenol (0.210 g, 2.23 mmol, 1 eq.) and L-alanine methyl ester hydrogen chloride (0.261 g, 1.87 mmol, 1 eq.) to give product 8a (0.150 g, 24%) as a colorless oil. $\delta_P$ NMR (202 MHz, $CDCl_3$): 9.05 (dd, J=101.1, 49.9), 8.41 (dd, J=100.0, 51.1 Hz). $\delta_H$ NMR (500 MHz, $CDCl_3$): 7.35 (m, 2H, Ar), 7.21 (m, 3H, Ar), 5.89 (m, 1H, $CH_2$=CH), 5.29 (m, $CH_2$=CH), 4.14 (m, 1H, CH—NH), 3.69 (d, J=6.6 Hz, 3H, $OCH_3$), 3.64 (m, 1H, NH), 3.13-2.84 (m, 2H, =CH—$CH_2$), 1.38 (2×d, 7.1 Hz, 3H, CH—CH). $\delta_C$ NMR (126 MHz, $CDCl_3$): 173.76 (d, J=4.1 Hz, C=O), 130.02 (d, J=4.1 Hz), 127.40-127.07 (m), 125.64, 121.54 (d, J=9.3 Hz), 120.54 (t, J=4.8 Hz), 52.69, 50.09 (d, J=6.6 Hz), 39.39-37.22 (m), 21.74 (2d, J=3.5 Hz, $CH_3$).

Isopropyl ((1,1-difluorobut-3-en-1-yl)(phenoxy)phosphoryl)-L-alaninate (8b). Synthesised following general procedure 1 using phenol (0.210 g, 2.23 mmol, 1 eq.) and L-alanine isopropyl ester hydrogen chloride (0.314 g, 1.87 mmol, 1 eq.) to give product 8b (0.165 g, 25%) as a colorless oil. $\delta_P$ NMR (202 MHz, $CDCl_3$): 9.17 (dd, J=101.1, 30.3 Hz), 8.46 (dd, J=99.9, 38.0 Hz). $\delta_H$ NMR (500 MHz, $CDCl_3$). 7.34 (m, 2H, Ar), 7.20 (m, 3H, Ar), 5.89 (m, 1H, $CH_2$=CH), 5.29 (m, 2H, $CH_2$=CH), 4.99 (m, 1H, CH-iPr), 4.14-3.99 (m, 1H, CH—NH), 3.68 (m, 1H, NH), 3.00-2.89 (m, 2H, =CH—$CH_2$), 1.35-1.17 (m, 9H, $CH_3$—CH—NH, CH-iPr). $\delta_C$ NMR (126 MHz, $CDCl_3$): 172.68 (d, J=5.9 Hz, C=O), 149.46, 129.88 (d, J=4.2 Hz), 127.11 (d, J=5.4 Hz), 125.46, 121.36 (d, J=8.9 Hz), 120.40 (t, J=4.9 Hz), 69.39 (d, J=2.8 Hz, CHiPr), 50.15, 38.63-37.99 (m), 21.58 (d, J=1.6 Hz), 21.44 (2 d, J=3.2 Hz, $CHCH_3$).

tert-Butyl ((1,1-difluorobut-3-en-1-yl)(phenoxy)phosphoryl)-L-alaninate (8c). Synthesised following general procedure 1 using phenol (0.210 g, 2.23 mmol, 1 eq.) and L-alanine tertbutyl ester hydrogen chloride (0.340 g, 1.87 mmol, 1 eq.) to give product 8c (0.320 g, 46%) as a colorless oil. $\delta_P$ NMR (202 MHz, $CDCl_3$): 9.23 (dd, J=101.0, 34.4 Hz), 8.52 (dd, J=99.6, 36.0 Hz). $\delta_H$ NMR (500 MHz, $CDCl_3$): 7.34 (m, 2H, Ar), 7.21 (m, 3H, Ar), 5.89 (m, 1H, $CH_2$=CH), 5.28 (m, 2H, $CH_2$=CH), 4.08-3.98 (m, 1H, CH—NH), 3.67 (m, 1H, NH), 3.01-2.84 (m, 2H, =CH—$CH_2$), 1.42 (d, J=5.2 Hz, 9H, tBu), 1.30 (d, J=7.2 Hz, 3H, CH—$CH_3$). $\delta_C$ NMR (126 MHz, $CDCl_3$): 172.48 (d, J=4.5 Hz, C=O), 149.72, 129.99 (d, J=2.1 Hz), 128.59-126.95 (m), 125.54, 121.46 (d, J=9.2 Hz), 120.54 (t, J=4.8 Hz), 82.32 (d, J=5.8 Hz), 50.69 (d, J=2.8 Hz, CH—NH), 38.80-38.12 (m), 27.99, 21.85 (2 d, J=3.1 Hz, $CHCH_3$).

Benzyl ((1,1-difluorobut-3-en-1-yl)(phenoxy)phosphoryl)-L-alaninate (8d). Synthesised following general procedure 1 using phenol (0.210 g, 2.23 mmol, 1 eq.) and L-alanine benzyl ester hydrogen chloride (0.403 g, 1.87 mmol, 1 eq.) to give product 8d (0.350 g, 45% yield) as a colorless oil. $\delta_P$ NMR (202 MHz, $CDCl_3$): 9.08 (dd, J=101.2, 45.4 Hz), 8.39 (dd, J=100.1, 46.5 Hz). $\delta_H$ NMR (500 MHz, $CDCl_3$): 7.41-7.29 (m, 7H, Ar), 7.25-7.17 (m, 3H, Ar), 5.87 (m, 1H, $CH_2$=CH), 5.27 (m, 2H, $CH_2$=CH), 5.11 (m, 2H, —$OCH_2$), 4.33-4.09 (m, 1H, CH—NH), 3.68 (m, 1H, NH), 2.93 (m, 2H, P—$CH_2$), 1.36 (d, J=7.2 Hz, 3H, CH—$CH_3$). $\delta_C$ NMR (126 MHz, $CDCl_3$): 173.15 (d, J=3.2 Hz, C=O), 149.68, 135.26 (d, J=6.4 Hz), 130.01 (d, J=4.1 Hz), 128.87-128.52 (m), 128.35 (d, J=1.1 Hz), 127.38-127.03 (m), 125.62, 122.24-120.38 (m), 120.51, 67.49, 50.20, 38.74-38.07 (m), 21.96 (2 d, J=3.5 Hz, $CHCH_3$).

Methyl (((E)-1,1-difluoro-5-hydroxy-4-methylpent-3-en-1-yl)(phenoxy)phosphoryl)-L-alaninate (9a). Synthesised following general procedure 2 using 8a (0.150 g, 0.45 mmol, 1 eq.) to give product 9a (97 mg, 58%) as a colorless oil. $\delta_P$ NMR (202 MHz, $CDCl_3$) δ 9.27 (dd, J=112.1, 18.4 Hz), 8.44 (dd, J=126.4, 20.2 Hz). $\delta_H$ NMR (500 MHz, $CDCl_3$): 7.35 (m, 2H, Ar), 7.21 (m, 3H, Ar), 5.56 (m, 1H, =CH), 4.18 (m, 1H, CH—NH), 4.07 (m, 2H, =CH—$CH_2$), 3.75-3.46 (m, 4H, NH, $OCH_3$), 3.10-2.79 (m, 2H, =CH—$CH_2$), 1.83 (m, 1H, OH), 1.76 (s, 3H, $CH_3(CH_2)C$=CH), 1.37 (2×d, J=7.1 Hz, 3H, CH—$CH_3$). $\delta_C$ NMR (126 MHz, $CDCl_3$): 176.76, 141.38 (d, J=7.6 Hz), 130.04 (d, J=3.2 Hz), 125.65 (d, J=4.0 Hz), 120.56 (d, J=4.6 Hz), 120.47 (d, J=4.7 Hz), 68.25 (d, J=1.9 Hz), 52.80 ($CH_3$—O), 50.09 (d, J=4.1 Hz, CH—NH), 32.82, 21.82 (2 d, J=2.6 Hz, $CHCH_3$), 14.15 ($CH_3$). HRMS (ES+, m/z) calcd. for (M+Na)+ $C_{16}H_{22}F_2NO_5NaP$: 400.1101; found: 400.1109.

Isopropyl (((E)-1,1-difluoro-5-hydroxy-4-methylpent-3-en-1-yl)(phenoxy)phosphoryl)-L-alaninate (9b). Synthesised following general procedure 2 using 8b (0.150 g, 0.41 mmol, 1 eq.) to give product 9b (117 mg, 69%) as a colorless oil. $\delta_P$ NMR (202 MHz, $CDCl_3$): 9.30 (dd, J=109.1, 34.4 Hz), 8.42 (dd, J=111.1, 38.4 Hz). $\delta_H$ NMR (500 MHz, $CDCl_3$): 7.35 (m, 2H, Ar), 7.21 (m, 3H, Ar), 5.56 (m, 1H, =CH), 5.00 (m, 1H, CH-iPr), 4.17-3.91 (m, 3H, CH—NH, =CH—$CH_2$), 3.67 (m, 1H, NH), 3.08-2.75 (m, 2H, =CH—$CH_2$), 1.86 (m, 1H, OH), 1.70 (s, 3H, $CH_3(CH_2)$C=CH), 1.34-1.19 (m, 9H, $CH_3$—CH—NH, CH-iPr). $\delta_C$ NMR (126 MHz, $CDCl_3$): 173.09 (d, J=6.8 Hz, C=O), 141.37 (d, J=7.9 Hz), 130.03 (d, J=2.6 Hz), 125.60 (d, J=4.4 Hz), 120.50 (dd, J=10.6, 4.7 Hz), 113.79-113.43 (m), 69.71 (d, J=4.5 Hz), 68.25, 50.29 (d, J=9.6 Hz), 30.88-28.72 (m), 21.73 (d, J=8.2 Hz), 21.84 (2d, J=4.1 Hz, $CHCH_3$), 14.18 ($CH_3$). HRMS (ES+, m/z) calcd. for (M+Na)+ $C_{18}H_{26}F_2NO_5NaP$: 428.1414; found: 428.1414.

tert-Butyl (((E)-1,1-difluoro-5-hydroxy-4-methylpent-3-en-1-yl)(phenoxy)phosphoryl)-L-alaninate (9c). Synthesised following general procedure 2 using 8c (0.150 g, 0.39 mmol, 1 eq.) to give product 9c (105 mg, 63%) as a colorless oil. $\delta_P$ NMR (202 MHz, $CDCl_3$): 9.36 (dd, J=109.1, 34.4 Hz), 8.48 (dd, J=111.1, 36.4 Hz). $\delta_H$ NMR (500 MHz, $CDCl_3$): 7.36 (m, 2H, Ar), 7.22 (m, 3H, Ar), 5.56 (m, 1H, =CH), 4.16-3.93 (m, 3H, CH—NH, =CH—$CH_2$), 3.63 (m, 1H, NH), 3.08-2.77 (m, 2H, =CH—$CH_2$), 1.90 (m, 1H, OH), 1.71 (s, 3H, $CH_3(CH_2)C$=CH), 1.43 (d, J=5.2 Hz, 9H, t Bu), 1.30 (2×d, J=7.1 Hz, 3H, CH—$CH_3$). $\delta_C$ NMR (126 MHz, $CDCl_3$): 172.79 (d, J=6.8 Hz, C=O), 130.02, 125.56 (d, J=5.8 Hz), 120.55 (d, J=4.6 Hz), 120.47 (d, J=4.4 Hz), 82.59, 68.26, 50.72 (d, J=7.4 Hz, CH—NH), 32.97-32.80 (m), 28.02 (d, J=1.1 Hz, 3×$CH_3$), 21.98 (2 d, J=3.8 Hz, $CHCH_3$), 14.16. HRMS (ES+, m/z) calcd. for (M+Na)+ $C_{19}H_{28}F_2NO_5NaP$: 442.1571; found: 442.1578.

Benzyl WE)-1,1-difluoro-5-hydroxy-4-methylpent-3-en-1-yl)(phenoxy)phosphoryl)-L-alaninate (9d). Synthesised following general procedure 2 using 8d (0.150 g, 0.36 mmol, 1 eq.) to give product 9d (101 mg, 61%) as a colorless oil. $\delta_P$ NMR (202 MHz, $CDCl_3$): 9.21 (dd, J=113.2, 22.3 Hz), 8.37 (dd, J=111.1, 24.3 Hz). $\delta_H$ NMR (500 MHz, $CDCl_3$): 7.39-7.28 (m, 7H, Ar), 7.24-7.16 (m, 3H, Ar), 5.55 (m, 1H, =CH), 5.13 (m, 2H, $OCH_2$), 4.27-4.14 (m, 1H, CH—NH), 4.06 (m, 2H, =CH—$CH_2$), 3.68 (m, 1H, NH), 3.05-2.73 (m, 2H, =CH—$CH_2$), 1.80 (m, 1H, OH), 1.69 (s, 3H, $CH_3(CH_2)C$=CH), 1.35 (2×d, J=7.1 Hz, 3H, CH—$CH_3$). $\delta_C$ (126 MHz, $CDCl_3$): 173.38 (d, J=7.9 Hz, C=O), 149.71, 141.37 (d, J=8.3 Hz), 130.04 (d, J=3.1 Hz), 128.76 (d, J=12.8 Hz), 128.35 (s), 125.63 (d, J=5.5 Hz), 120.49 (dd, J=13.7, 4.6 Hz), 113.75-113.34 (m), 68.25 (d, J=2.4 Hz), 67.61, 50.22 (d, J=8.0 Hz), 34.32-31.18 (m), 21.84 (d, J=3.8 Hz, $CHCH_3$), 14.15 ($CH_3$). HRMS (ES+, m/z) calcd. for (M+Na)+ $C_{22}H_{26}F_2NO_5NaP$: 476.1414; found: 476.1421.

Cell Isolation

Blood was obtained in the presence of a mixture of Heparin and Ethylenediaminetetraacetic acid (EDTA) as anticoagulants (2 U/ml heparin, 1.5 mM EDTA) from consented healthy donors (approved by the NRES Committee West Midlands ethical board; REC reference 14/WM/1254). Blood was then layered on a density gradient medium, lymphoprep (Stem Cell Technologies) and Peripheral blood mononuclear cells (PBMCs) were purified by gradient centrifugation. The cells were washed 2 times with Phosphate Buffered Saline (PBS), then resuspended in RPMI-1640 media supplemented with 2 mM L-glutamine, 25 mM HEPES, 1% sodium pyruvate, 50 μg/ml penicillin/streptomycin (Invitrogen) and 10% foetal calf serum.

Flow Cytometric Analysis

Untreated and treated PBMCs were labelled with Zombie aqua viability dye (Biolegend) and subsequently were stained with a mixture of BV421-conjugated anti-CD3 (UCHT1, Biolegend), BV650-conjugated anti-CD8 (SK1; BD Bioscience), FITC-conjugated anti-CD25 (M-A25, Biolegend), PE-conjugated anti-CD69 (TP1.55.3; Beckman Coulter) and PE Cy5-conjugated anti-Vγ9 TCR (IMMU360, Beckman Coulter) and APC-conjugated anti-Vδ2 TCR (123R3, Miltenyi Biotech) antibodies. The percentages of $CD69^+CD25^+$ within $CD8^+$ T cell subset or Vγ9Vδ2 T-cell population were measured using flow cytometer. Data were analysed using FlowJo V10 software.

Cytotoxicity Assay

Vγ9Vδ2 T cells were expanded from PBMCs in the presence of 5 μM zoledronate for 14 days and 100 U/ml IL-2 (Peprotech) was added into the media every 2-3 days, yielding ~85% Vγ9Vδ2 T cells. Bladder carcinoma cell line, T24 (ATCC HTB4) were labelled with 0.1 μM CFSE and incubated for 4 hours with 10 μM zoledronate, 100 μM of HMBPP or 100 μM of the indicated prodrugs, before being washed five-times in medium and co-cultured with previously expanded Vγ9Vδ2 T cells in an effector target ratio of 10:1 for 18 hours. All cells were then labelled with eFluor780 viability dye and $CFSE^+$ eFluor780 viability $dye^+$ cells were measured using flow cytometry. Data were analysed using FlowJo V10.

REFERENCES

1. Morita, C. T.; Jin, C.; Sarikonda, G.; Wang, H. Nonpeptide antigens, presentation mechanisms, and immunological memory of human Vgamma2Vdelta2 T cells: discriminating friend from foe through the recognition of prenyl pyrophosphate antigens. *Immunol Rev* 2007, 215, 59-76.
2. Shen, Y.; Zhou, D.; Qiu, L.; Lai, X.; Simon, M.; Shen, L.; Kou, Z.; Wang, Q.; Jiang, L.; Estep, J.; Hunt, R.; Clagett, M.; Sehgal, P. K.; Li, Y.; Zeng, X.; Morita, C. T.; Brenner, M. B.; Letvin, N. L.; Chen, Z. W. Adaptive immune response of Vgamma2Vdelta2+ T cells during mycobacterial infections. *Science* (New York, N.Y.) 2002, 295, 2255-8.
3. Fisher, J. P.; Heuijerjans, J.; Yan, M.; Gustafsson, K.; Anderson, J. gammadelta T cells for cancer immunotherapy: A systematic review of clinical trials. *Oncoimmunology* 2014, 3, e27572.
4. Maraka, S.; Kennel, K. A. Bisphosphonates for the prevention and treatment of osteoporosis. *BMJ* (*Clinical research ed.*) 2015, 351, h3783.
5. Roelofs, A. J.; Jauhiainen, M.; Monkkonen, H.; Rogers, M. J.; Monkkonen, J.; Thompson, K. Peripheral blood monocytes are responsible for gammadelta T cell activation induced by zoledronic acid through accumulation of IPP/DMAPP. *British journal of haematology* 2009, 144, 245-50.
6. Davey, M. S.; Malde, R.; Mykura, R. C.; Baker, A. T.; Taher, T. E.; Le Duff, C. S.; Willcox, B. E.; Mehellou, Y. Synthesis and Biological Evaluation of (E)-4-Hydroxy-3-methylbut-2-enyl Phosphate (HMBP) Aryloxy Triester Phosphoramidate Prodrugs as Activators of Vgamma9/Vdelta2 T-Cell Immune Responses. *J Med Chem* 2018, 61, 2111-2117.
7. Vougioukalakis, G. C.; Grubbs, R. H. Ruthenium-based heterocyclic carbene-coordinated olefin metathesis catalysts. *Chem Rev* 2010, 110, 1746-87.
8. McKenna, C. E.; Higa, M. T.; Cheung, N. H.; McKenna, M.-C. The facile dealkylation of phosphonic acid dialkyl esters by bromotrimethylsilane. *Tetrahedron Letters* 1977, 18, 155-158.
9. Bessieres, M.; Sari, O.; Roy, V.; Warszycki, D.; Bojarski, A. J.; Nolan, S. P.; Snoeck, R.; Andrei, G.; Schinazi, R. F.; Agrofoglio, L. A. Sonication-Assisted Synthesis of (E)-2-Methyl-but-2-enyl Nucleoside Phosphonate Prodrugs. *ChemistrySelect* 2016, 1, 3108-3813.
10. Mehellou, Y. The ProTides Boom. *ChemMedChem* 2016, 11, 1114-6.
11. Osgerby, L.; Lai, Y. C.; Thornton, P. J.; Amalfitano, J.; Le Duff, C. S.; Jabeen, I.; Kadri, H.; Miccoli, A.; Tucker, J. H. R.; Muqit, M. M. K.; Mehellou, Y. Kinetin Riboside and Its ProTides Activate the Parkinson's Disease Associated PTEN-Induced Putative Kinase 1 (PINK1) Independent of Mitochondrial Depolarization. *J Med Chem* 2017, 60, 3518-3524.

The invention claimed is:

1. A compound according to Formula (IV) including all tautomers thereof, (IV)

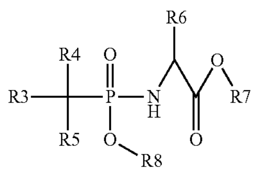

wherein:

R3 is a radical according to Formula (V), Formula (VI) or Formula (VII), (V)

(VI)

(VII)

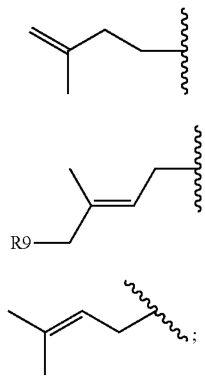

R9 is OH, and each of R4 and R5 independently represent H or halo;

R6 is a $C_{1-4}$ alkyl chain;

R7 is a $C_{6-14}$ aryl group or a benzyl group;

R8 represents an optionally substituted $C_{5-25}$ aryl or a 5 to 25 membered heteroaryl group;

or a salt thereof.

2. A compound according to claim 1, wherein one or both, of R4 and R5 represent halo.

3. A compound according to claim 2, wherein said halo substituents is/are fluoro.

4. A compound according to claim 1, selected from the group consisting of:

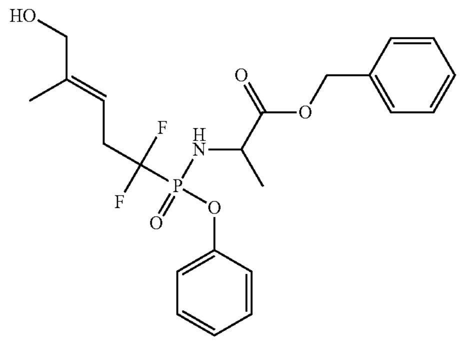

-continued

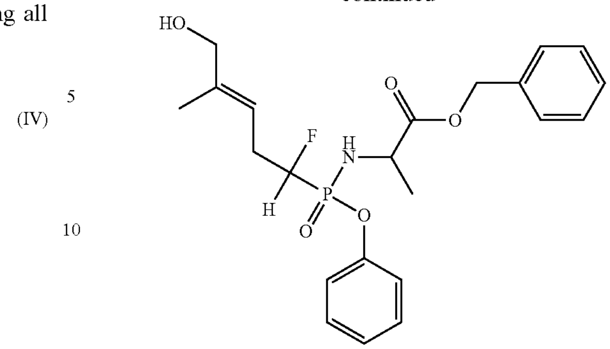

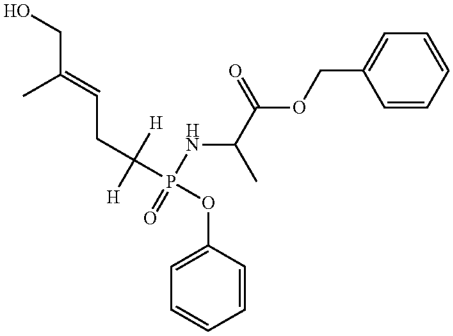

5. A pharmaceutical composition comprising a compound as defined in claim 1 and a pharmaceutically acceptable excipient or carrier.

6. A compound according to claim 1, wherein R7 is a $C_{6-10}$ aryl group.

7. A compound according to claim 1, wherein R7 is a benzyl group.

8. A compound according to claim 7, wherein R7 is an unsubstituted benzyl group.

9. A method of inducing proliferation of γδ T cells, said method comprising ex vivo mixing the compound of claim 1 with a sample of γδ T cells.

10. A method of inducing proliferation of γδ T cells, said method comprising ex vivo mixing the composition of claim 5 with a sample of γδ T cells.

* * * * *